United States Patent [19]

Southgate et al.

[11] Patent Number: 5,863,801

[45] Date of Patent: Jan. 26, 1999

[54] AUTOMATED NUCLEIC ACID ISOLATION

[75] Inventors: Peter David Southgate, Monmouth Junction; Zvi Gerald Loewy, Bergen, both of N.J.

[73] Assignee: Sarnoff Corporation, Princeton, N.J.

[21] Appl. No.: 664,780

[22] Filed: Jun. 14, 1996

[51] Int. Cl.[6] .................................................. G01N 33/48
[52] U.S. Cl. ..................... 436/63; 436/177; 436/178; 422/68.1; 422/99; 422/101; 422/102; 422/104; 422/939; 422/942; 422/948; 435/285.1; 435/287.2; 435/287.3; 435/288.3; 435/288.5; 435/305.1; 435/306.1; 935/85
[58] Field of Search .............................. 436/63, 174, 175, 436/177, 178; 422/67, 68.1, 99, 101, 102–104, 939, 940, 942, 947, 948; 935/85–87; 435/283.1, 285.1, 287.2, 287.3, 288.2, 288.3, 288.4, 288.5, 302.1, 305.1, 305.2, 306.1

[56] References Cited

U.S. PATENT DOCUMENTS

| | | | |
|---|---|---|---|
| 5,100,626 | 3/1992 | Levin | 422/101 X |
| 5,114,858 | 5/1992 | Williams et al. | 435/270 |
| 5,346,999 | 9/1994 | Cathcart et al. | 436/175 X |
| 5,498,392 | 3/1996 | Wilding et al. | 422/68.1 |

FOREIGN PATENT DOCUMENTS

| | | |
|---|---|---|
| 0487028 | 5/1992 | European Pat. Off. . |
| 92/15597 | 9/1992 | WIPO . |

OTHER PUBLICATIONS

Shofi et al., *Electronic and Communications* in Japan, Part 2, 72(10):52–59 (1989).
Esashi et al., *Sensors and Actuators*, 20:163–169 (1989).

*Primary Examiner*—Maureen M. Wallenhorst
*Attorney, Agent, or Firm*—William J. Burke

[57] ABSTRACT

The present invention relates to a device and a method of use for that device for the automated preparation of nucleic acid from a biological sample. The device relates to a cassette in which all chemical manipulations occur, which includes a storage/transfer strip where the prepared nucleic acid is deposited and stored without contamination. Moreover, the waste of the preparation protocol is contained in the cassette, which, upon the separation of the filled storage/transfer strip is completely sealed off from the environment. In a preferred embodiment, the inventive device can prepare nucleic acid preparations from up to 24 different biological samples at a time.

43 Claims, 8 Drawing Sheets

AUTOMATED NUCLEIC ACID ISOLATION

This invention was made with U.S. Government support under Contract No. 70NANB5H1037. The U.S. Government has certain rights in this invention.

This patent application is being concurrently filed with the following related U.S. patent applications: METHOD FOR POLYNUCLEOTIDE SEQUENCING, R. Kumar and P. Heaney, inventors, Attorney Docket No. DSRC/12024, U.S. Ser. No. 08/605,210, now abandoned in favor of application Ser. No. 08/950,709; NUCLEASE PROTECTION ASSAYS, R. Kumar, inventor, Attorney Docket No. DSRC/12038, U.S. Ser. No. 08/665,104 now U.S. Pat. No. 5,770,370 issued on Jun. 23, 1998; MICROFLUIDIC METHOD FOR NUCLEIC ACID AMPLIFICATION, Z. Loewy and R. Kumar, inventors, Attorney Docket No. DSRC/12050, U.S. Ser. No. 665,209; METHOD FOR AMPLIFYING A POLYNUCLEOTIDE, Z. Loewy, inventor, Attorney Docket No. DSRC/12081, U.S. Ser. No. 663,688; PADLOCK PROBE DETECTION, R. Kumar, inventor, Attorney Docket No. DSRC/12162, U.S. Ser. No. 08/665,208. This patent application is related to the following copending U.S. patent applications: U.S. Ser. No. 60/009,517, filed Nov. 3, 1995, Attorney Docket No. DSRC/11772 now U.S. Ser. No. 08/742,317; U.S. Ser. No. 60/006,202, filed Nov. 3, 1995, Attorney Docket No. DSRC/11904 now U.S. Ser. No. 08/742,971; and U.S. Ser. No. 60/010,513, filed Jan. 24, 1996, Attorney Docket No. DSRC/11895 now U.S. Ser. No. 08/786,956.

The present invention relates to the field of nucleic acid analysis, and in particular, to the isolation of nucleic acid from a biological or clinical specimen, wherein the nucleic acid is used for testing purposes.

Isolation of nucleic acid from a biological sample is a time-consuming, tedious process, requiring a series of steps that are common to such isolation from virtually any source of nucleic acid. For genetic analysis regarding genetic-based disease, conditions, or characteristics, it is essential to have available a reliable, easily reproduced method of nucleic acid isolation, particularly one that is amenable to automation.

Such analysis can be with respect to sequence variation in a particular gene that correlates to a particular inborn disease, such as, for example, sickle-cell anemia or Tay-Sachs disease, or to a particular inborn condition, such as, for example, susceptibility to heart disease or breast cancer. Additionally, such analysis can be with respect to yet other sequences of nucleic acid that are not necessarily assigned as to gene function, but which can be useful as forensic evidence for purposes of identification of an individual. One can also diagnose certain diseases based on the expression of a particular gene, ascertaining misplaced or mistimed genetic expression that correlates to a given disease or condition, such as metastasized cancer, or infertility. Such analysis can also be used to detect infection by external agents, such as a pathogenic bacterium responsible for, for example, diphtheria (Corynebacteriaceae), pneumonia (Diplococcus), meningitis (Neisseria), or gonnorhea (Nesseria), or a virus responsible for AIDS (human immunodeficiency virus) or hepatitis (caused by one of the ever-expanding varieties of hepatitis viruses). Genetic analysis also has an expanding role in forensic evidence, such as providing a connection between blood or semen and a victim or alleged rapist.

A common requirement for assuring or increasing the reliability of any of the aforementioned forms of genetic and nucleic acid analysis is that the source tissue must be processed for isolation of the included nucleic acids using standard, uniformly-performed procedures suitable for their respective measurement. Difficulties that need to be considered and overcome is that the technician effecting the nucleic acid isolation must not inadvertently contaminate the biological or clinical sample being processed, or otherwise damage the sample. As important, especially in the conduct of pathogen or forensic analysis, methods and materials are needed to allow a technician to isolate the nucleic acid without getting contaminated himself or herself. A further difficulty, particularly in the conduct of forensic analysis, is that the biological sample on which the procedure is to be performed can be exceedingly small, such as nanoliter or nanogram quantities or less.

Therefore, there is a need for a method and materials therefor for isolating nucleic acid such that any ordinarily skilled technician can use the method and materials and provide nucleic acid compositions from a biological or clinical sample. Such a method and materials therefor preferably would have safeguards in place to minimize the possibility of contamination by or to the technician. Such a method and materials would also be geared for preparing nucleic acid compositions from very small samples, such as those containing less than a nanogram of nucleic acid, as described hereinbelow.

SUMMARY OF THE INVENTION

The present invention relates to a method and a device for performing that method for the automated isolation of nucleic acid from a biological sample. Accordingly, in one embodiment of the invention, a device for nucleic acid extraction from one or more biological samples comprising a removable cassette, wherein the cassette comprises a separable sample transfer/storage strip is set forth herein. The cassette of the invention can be sealed or open, preferably it is sealed. The preferred cassette also has a movable input transfer bar, and is encased in a caddy. More particularly, the device of the present invention incorporates a cassette further comprising (1) a hollow body having a top side, an exterior, an interior, at least one slot for the placement of the cassette, and at least one well for the placement of a sample container. Additionally, the cassette includes a means for moving the cassette from or into the caddy, as well as a means for activating the input transfer sample bar. The preferred device also comprises an air nozzle in communication with means for accessing, storing, or generating pressurized air, and a means for sealing sample input channels of the cassette. Furthermore, the device includes valve actuators located in the interior for opening and closing valves in the cassette, and one or more pump actuators for moving fluid in or out of fluid chambers in the cassette. The device of the present invention also preferably includes a magnet, a power supply, a user interface, and a bar-code reading means. Preferably, the device of the present invention also comprises a sensor means in the slot or well, which signals that the slot or well is occupied when a cassette or sample container has been respectively inserted therein. In another embodiment, the device of the present invention further comprises a memory means. In yet another embodiment, the device further comprises a separating means for separating the strip from the remainder of the cassette. The separating means is preferably a knife having a heating means in communication thereto, the use of which seals both the strip and the remainder of the cassette. The preferred device has more than one well; more preferred, the device has about 24 wells and about 4 slots; more preferred yet, the device has at least about 24 wells and at least about 4 slots. The device preferably includes the cassette that further comprises:

(1) one or more sample entry ports located on the input transfer sample bar that are serially and respectively in communication with the same number of wells of the device, wherein the ports are also in communication with input sample storage reservoirs of the cassette;

(2) one or more reaction flow-ways that are serially and respectively in communication via fluid exchange channels with the same number of sample input storage reservoirs;

(3) fluid chambers in communication with the fluid exchange channels, wherein fluid chambers are supply chambers for reagents, reservoirs for samples, or reaction chambers;

(4) valves for controlling the flow of fluids in the fluid exchange channels; and (5) a sample transfer/storage strip having at least one of the fluid chambers that is in communication with a reaction flow-way.

The preferred device is operated where two reaction flow-ways are dedicated to positive and negative control samples containing or not containing nucleic acid, respectively; wherein the input transfer sample bar comprises a first cannula that is an entry port and connects the sample container to the sample input channel and a second cannula that connects the same sample container to the air nozzle upon movement of the input transfer sample bar and engagement of same with the sample container; wherein the supply chamber is a chamber formed in a solid support and having a film, such as a Bursapak™ supply chamber, having a releasable seal blocking an outlet or outlets into the fluid exchange channels of the reaction flow-way; wherein at least one of the pump actuators comprises a foot-pad pump with foot-pads designed to push on the supply chambers to open the sealed outlets and pump fluid into the fluid exchange channels; wherein each of the supply chambers is collapsible upon evacuation and fillable from a vacuum-collapsed state to a defined volume; wherein the supply chambers store and deliver to the reaction flow-way a lysis reagent, microparticles, wash fluid, or buffer alone; wherein the lysis reagent is combined with microparticles; wherein the microparticles comprise a compound that binds specifically to nucleic acid or is paramagnetic; and wherein the transfer/storage strip transfers and stores nucleic acid extracted from each sample separately from one another.

In another embodiment, the present invention relates to a method for extracting nucleic acid from a biological sample using the aforementioned device, comprising providing the device for nucleic acid extraction from one or more biological samples and extracting the biological sample via the cassette. The preferred method includes the steps of:

(1) providing the device for nucleic acid extraction from one or more biological samples and extracting the biological sample via the cassette; and (2) inserting at least one caddy-encased or partially caddy-encased cassette into a slot on the device;

the preferred method further comprises (3) inserting one or more sample containers, each containing a biological sample for extraction, into a well on the device. An alternative preferred method of the present invention further comprises (4) applying air pressure by way of the second cannula to expel the biological sample from the sample container; and, in another preferred embodiment, additionally comprises (5) opening sample input valves thereby filling the input sample reservoirs. The preferred method also comprises including control biological samples, wherein a positive control including nucleic acid and a negative control including no nucleic acid are included; and further comprises delivering about 20 µl to about 200 µl of substantially purified nucleic acid solution or substantially purified nucleic acid complexed to microparticles into the sample storage/transfer strip; wherein the biological sample is selected from the group consisting of whole blood, plasma, serum, urine, and suspensions of swab or sputum; wherein steps for extracting the nucleic acid from the biological sample comprise:

(1) lysing of cells or other biological matter included in the biological sample in the presence of a surface having specific affinity for nucleic acid; and (2) substantially purifying the nucleic acid from the lysed biological sample;

wherein the surface is a paramagnetic microparticle; wherein dynamic data entries, dynamic process parameters, results, error information, location of well into which a given sample container was inserted, location of slot into which a given cassette was inserted, and correlating such entries to a bar-code identifier associated with a sample are captured and stored by the memory means; wherein two or more sample containers, each containing a biological sample, are each inserted into separate wells; and wherein the biological samples are extracted in parallel.

In yet another embodiment, the present invention relates to a chemistry cassette for extracting nucleic acid, comprising a separable sample transfer/storage strip, which cassette or transfer/storage strip or both can be sealed or not; and preferably is sealed. The cassette of the present invention further comprises a movable input sample transfer bar; further comprises:

(1) one or more sample entry ports located on the input transfer sample bar that are serially and respectively in communication with the same number of sample input metering chambers located in the cassette;

(2) one or more reaction flow-ways that are serially and respectively in communication via fluid exchange channels with the same number of sample input metering chambers;

(3) fluid chambers in communication with the fluid exchange channels, wherein fluid chambers are supply chambers for reagents, metering chambers for samples, or reaction chambers, and wherein the supply chambers store and deliver to the reaction flow-way a lysis reagent, microparticles in a buffer, or buffer alone for nucleic acid extraction; and (4) valves for controlling the flow of fluids in the fluid exchange channels;

wherein the sample transfer/storage strip includes at least one of the fluid chambers that is in communication with the reaction flow-way; wherein the input transfer sample bar comprises a first cannula that is an entry port and connects the sample container to the sample input channel and a second cannula that connects the same sample container to the air nozzle upon activation of the input sample transfer bar and engagement of same with the sample container; wherein the supply chamber is a Bursapak™ supply chamber having a releasable seal blocking an outlet or outlets into the fluid exchange channels of the reaction flow-ways; wherein each of the supply chambers is collapsible upon evacuation and fillable from a vacuum-collapsed state to a defined volume; wherein the lysis reagent is combined with microparticles; wherein the microparticles comprise a compound that has specific affinity for nucleic acid or is paramagnetic; wherein there are two or more sample entry ports and two or more reaction flow-ways; wherein the transfer/ storage strip transfers and stores nucleic acid extracted from each sample separately from one another; and wherein the separable transfer/storage strip is connected to the remainder of the cassette, which, upon being separated, seals both the strip and the remainder of the cassette.

DEFINITIONS

Figure 1:
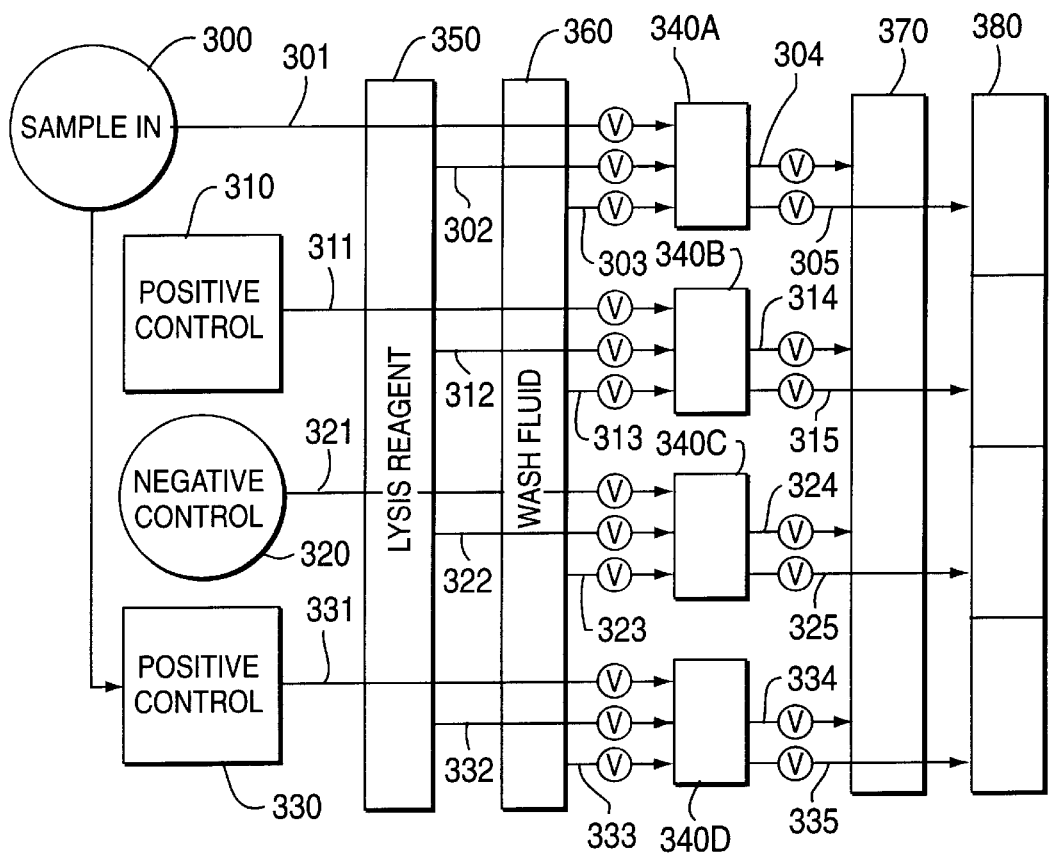
FIG. 1 is a schematic diagram of the method of nucleic acid preparation that is carried out within the confines of the cassette.

The following terms used in this disclosure shall have the meanings set forth below:

Bursapak™ chamber a chamber formed in a solid support and having a film formed of a flexible material that is sealed to the support at the edges of the chamber and has an outlet channel that is blocked by a portion of the film which is sealed over the outlet channel, wherein the seal over the outlet is broken or removed by pressurizing the fluid contents of the chamber at a pressure that does not affect the seal at the edges of the chamber; preferably, the film is on the upper face of the cassette body and the outlet channel is oriented downwards.

caddy a protective covering that can be removed, which fully or partially covers the cassette.

cassette a disposable device for conducting reactions therein having a cassette body, one or more upper membranes and one or more lower membranes which together define one or more supply chambers, one or more reaction chambers and fluid exchange channels connecting the supply chambers to reaction chambers.

cassette body a solid portion having sufficient depth and sturdiness to allow cavities formed therein to provide the depth for fluid chambers and fluid exchange channels.

collapsible upon evacuation some of the chambers described below will preferably be filled by first applying a vacuum to evacuate the chamber contents and then filling the evacuated chamber with fluid—preferably, these chambers are "collapsible" in that they have at least one flexible film that collapses to minimize chamber volume.

connection or communication two fluid chambers, inlets or detection channels are "connected" or have a "route of connection" or in "communication" therebetween if there is one or more fluid exchange channels joining the two such that fluid can move from one to the other.

concentric Bursapak™ supply chamber an internal outlet Bursapak supply chamber wherein the outlet channel is located substantially in the center of the supply chamber; "substantially in the center" means that the distance between the center of the supply chamber and the geometric center of the supply chamber is no more than about 20% of the length of the supply chamber cross-section defined by the line joining the center of the outlet and the geometric center of the supply center.

elevated pressure a pressure more than ambient atmospheric pressure.

fillable from a vacuum-collapsed state to a defined volume these are chambers that unfold from the collapsed state to a first volume; preferably, the inserted fluid volume is within about 10% of the first volume, more preferably within about 3% of the first volume. The first volume is the maximum volume of fluid that can be inserted into the chamber without affecting the integrity of the chamber.

fluid chamber the term "fluid chamber" encompasses reaction, supply, waste, metering and sample storage chambers, and other fluid containing chambers. In those embodiments where contents of the chambers can be pumped out using a foot-pad having a shape that conforms to a covering film that is inverted to match the shape of the bottom of the chamber, the chamber can be closed by maintaining the foot-pad pressed against the inverted covering film. In another embodiment, the fluid chamber is comprised of two covering films, which can be impressed upon from opposite sides by two foot pads, respectively, in the same fashion as for the simple-covering filmed fluid chambers.

fluid-tight a space or chamber is fluid-tight if it retains an aqueous fluid in the space at a temperature of 99° C. for one hour and experiences substantially no air diffusion therefrom or thereunto over one year at 4° C.; a seal between two materials is fluid-tight if the seal is substantially no more permeable to water than the most water-permeable such material.

foot-pad a plunger having a shape designed to conform to the inverted shape of the covering film of a supply chamber; when the plunger presses against the flexible film it pressurizes the fluid in the supply chamber and, if an exit is available, pushes the fluid out of the supply chamber.

foot-pad pump a mechanical, electromechanical or pneumatic device that uses a one or more, preferably two or more, foot-pads to press on one or more fluid chambers such as supply chambers or reaction chambers to pressurize the contents and push the contents out through an unobstructed connected fluid exchange channel.

internal control a nucleic acid added to a clinical specimen, wherein the nucleic acid includes sequences that are complementary to primers used to amplify a particular polynucleotide from the clinical specimen, but also includes other unique sequences that allow quantitation and an analysis of the efficiency of the amplification method.

integral parts or elements of a valve are integral to a body layer or to a cassette if they cannot be facilely and reversibly detached from that body layer or cassette.

internal outlet Bursapak™ supply chamber a Bursapak™ supply chamber wherein the outlet channel is located away from the edges of the supply chamber such that fluid-containing space is interposed between the sealed outlet channel and the edges chamber.

microparticle a microparticle can have any shape, which is preferably spherical. Preferably, it has a diameter of less than 1 mm, and more preferably, less than 500 microns. In certain preferred embodiments, the microparticles have a diameter from about 0.5 micron to about 25 microns, and more preferably from about 1 micron to about 5 microns, and even more preferably, about 2 microns to about 4 microns. Microparticles are comprised of any suitable material, the choice of material being guided by its characteristics, which preferably include minimal non-specific adsorptive characteristics, such as that of polystyrene. In other embodiments, the microparticles are comprised of, for example, plastic, glass, cellulose, a cellulose derivative, nylon, polytetrafluoroethylene ("TEFLON"), ceramic and the like. A paramagnetic bead can be comprised of, for example, iron dispersed in a polystyrene matrix, and can be obtained, for example, from Dynal (Oslo, Norway).

negative control a material designed to be comparable to a sample to be assayed but lacking the substance to be assayed for, such that a positive result upon assaying a negative control would indicate a problem with the assay protocol or assay reagents.

positive control a material designed to generate, in the absence of a problem with the assay chemistry such as the presence of an interfering substance, a positive assay result.

reaction chamber a fluid chamber for locating reactants undergoing or to undergo a reaction, comprised of any suitable material, i.e., a material that exhibits minimal non-specific adsorptivity or is treated to exhibit minimal non-specific adsorptivity, which material can be, for example, glass, plastic, nylon, ceramic, or combinations thereof, and is connected to at least two fluid exchange channels for passaging material in and out of the reaction chamber.

reaction flow-way a series of two or more serially connected fluid chambers through which fluids can move.

reduced pressure a pressure less than ambient atmospheric pressure.

sealed-chemistry cassette a cassette that includes fluid chambers for reagents, reactions, waste storage, etc., which is supplied in one embodiment only with a biological sample and from which only prepared nucleic acid is taken; in other embodiments, certain reagents and other fluids are introduced as well to what is otherwise a sealed instrument.

serially connected two or more fluid chambers are serially connected if there are fluid exchange channels by which fluid from a first of the serially connected chambers can pass to a second of the serially connected chambers, and from there to a third of the serially connected chambers, and so on until the fluid passes to the last of the serially connected chambers.

substantially uniform temperature in the reaction chamber where the temperature in a reaction chamber varies by no more than about ±0.3° C.

thermoelectric heat pump a device for heating and cooling fluid chambers that is made up of one or more thermoelectric blocks.

DETAILED DESCRIPTION

The present invention relates to a method for the isolation of nucleic acids contained in biological samples that solves the problem of variable results obtained when using conventional methods of nucleic acid isolation. The inventive method is characterized by the requirement of minimal hands-on input by any human operator, which is commonly (at least) the indirect source of the aforementioned variability. Accordingly, the steps of lysing tissue or cells of a biological sample and substantial retention of ribonucleic acid (RNA) or deoxyribonucleic acid (DNA), or combinations or subcategories thereof, to the substantial exclusion of other macromolecules and cell debris can be conducted in the context of the present invention in an automated or semi-automated manner. The nucleic acid analysis contemplated to be undertaken on the nucleic acid that is prepared in accordance with the present invention relates to hybridization or amplification for the identification of certain sequences of nucleic acid associated with a particular genetic-based disease or condition, or with a proportion of the population as used for forensic evidence, using methods known in the art. See, for example, *Short Protocols In Molecular Biology* (Ausubel et al., eds., 1992).

The method can be conceptualized as preferably taking the various aforementioned steps, all of which preferably take place in the confines of a cassette, which is fully described hereinbelow. Those steps are diagrammed schematically in FIG. 1. Presuming for the present that a single flow-way is provided as represented by the horizontal pathway emanating from the sample in port 300, the diagram demonstrates that (1) a fluid exchange channel 301 can be used as a conduit for a biological sample, (2) a second fluid exchange channel 302 can be used as a conduit for lysis reagent provided by a first supply chamber 350, (3) a third fluid exchange channel 303 can be used as a conduit for wash fluid 360 into reaction chamber 340A containing a substrate that selectively and releasably binds nucleic acid, (4) a fourth fluid exchange channel 304 can be used as a conduit for spent reagent or fluid into waste receptacle 370, and (5) a fifth fluid exchange channel 305 can be used as a conduit for the isolated nucleic acid into the storage/transfer strip 380, using pumps that are in place and actuated as appropriate and the respective valves (represented by an encircled letter "v") are open or closed as appropriate, which valve openings can be timed to allow for different time periods for lysing, washing, and transporting the isolated nucleic acid.

A nucleic acid is "isolated" in accordance with the invention in that the method or device employing that method of the invention acts on a biological sample that includes nucleic acid, such as a tissue or a cell, and isolates therefrom nucleic acids derived from the cell. This isolated nucleic acid may be substantially purified from other macromolecules and cell debris and contain the set of different polynucleotides found in a cell or tissue; alternatively, the isolated nucleic acid can be further separated into subclasses of nucleic acid, such as DNA alone, or RNA alone, or mRNA alone, and the like, thereby forming the various sorts of nucleic acid compositions. A nucleic acid composition is "substantially pure" in accordance with the invention if it is predominantly free of other macromolecules, i.e., the nucleic acid as a whole, or the particular nucleic acid type, constitutes at least about 50% by weight of the macromolecules in a composition. Preferably, the nucleic acid of the present invention constitutes at least about 60% by weight of the total macromolecules that are present in a given composition thereof, more preferably about 80%, still more preferably about 90%, yet more preferably about 95%, and most preferably about 100%. Such compositions are referred to herein as being nucleic acids that are 60% pure, 80% pure, 90% pure, 95% pure, or 100% pure, any of which are substantially pure.

Returning to FIG. 1, one can see that the figure presents a diagrammatical representation of the method where different samples, or a sample and various positive and negative controls, are subjected to the inventive method in parallel. In the embodiment represented by FIG. 1 as a whole, four flow-ways are shown, whereby nucleic acid from sample alone 300 is isolated (as just discussed) in reaction chamber 340A, a positive control 310 is prepared in reaction chamber 340B (wherein a known amount of nucleic acid is processed in parallel fashion), a negative control 320 is prepared in reaction chamber 340C (wherein a null amount of nucleic acid is processed, again in parallel fashion), and an internal control 330 is prepared in reaction chamber 340D (wherein a known amount of nucleic acid is processed in combination with the biological sample 300). All of the analogous fluid exchange channels and valves operate and serve the same functions as in the case just described for the biological sample 300 alone, i.e., the conduits provided by fluid exchange channels 301–305 operate in analogous manner to those of 311–315, 321–325, and 331–335, respectively. Resultant volumes of wash fluid containing nucleic acid (or not in the case of the negative control and not or lower than expected concentrations thereof in failed experimental and positive controls) are preferably caused to flow into individual compartments of the storage/transfer strip 380.

Figure 7A:
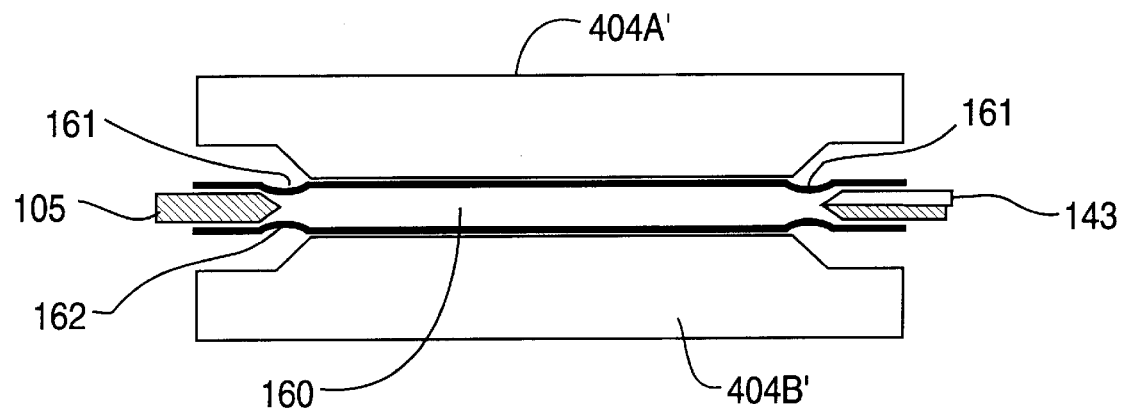
FIGS. 7A and 7B show the operation of a foot-pad pump on a reaction chamber.
Figure 7B:
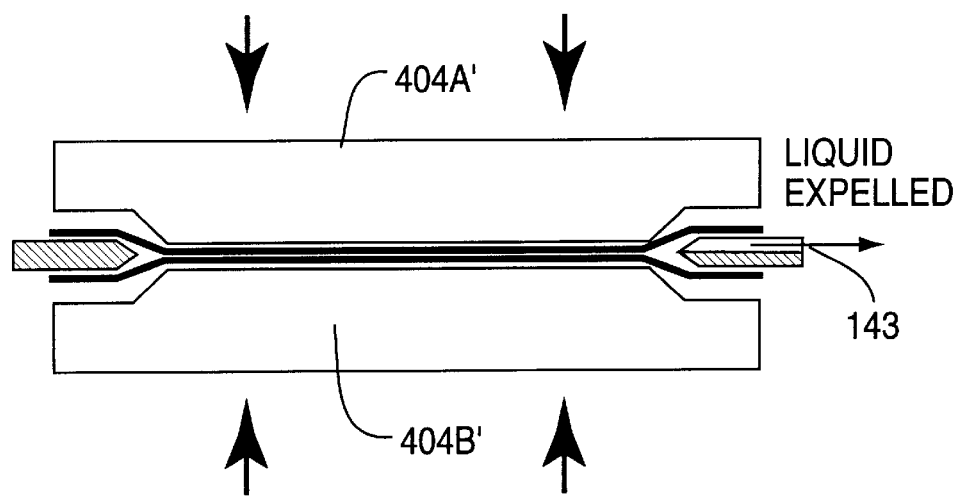

Some of the arrows in FIG. 1 that represent fluid exchange channels appear to pass through fluid chamber 350 or 360. These channels actually pass above or below the fluid chamber, as is described further in the text below. As is described further below, reaction chambers 340A–B preferably have a flexible upper film and lower film that can be manipulated with a foot-pad pump (see FIGS. 7A and 7B, wherein the action of the pressure caused by the foot-pad pump is illustrated, with liquid being expelled from the fluid chamber formed by the films 161 and 162 into the fluid exchange channel 143) or a gas pressure flow control means. If both upper and lower walls of a fluid chamber are formed with films, then channels passing through the region of the device occupied by the reaction chambers must pass adjacent to such chambers rather than above or below the chambers.

Pumping action can also be achieved using, for instance, peristaltic pumps, mechanisms whereby a roller pushes down on the flexible film of a fluid chamber to reduce the volume of the chamber, plungers that press on the flexible film of a fluid chamber to reduce its volume, and other pumping schemes known to the art. Such mechanisms include micro-electromechanical devices such as reported by Shoji et al., "Fabrication of a Pump for Integrated Chemical Analyzing Systems," *Electronics and Communications in Japan,* Part 2, 70, 52–59 (1989) or Esashi et al., "Normally closed microvalve and pump fabricated on a Silicon Wafer," *Sensors and Actuators,* 20, 163–169 (1989).

Preferably, the inventive method is designed to provide the prepared nucleic acid in volumes that correspond to the volume requirements of existing or future systems for the analysis of nucleic acids, such as the Abbott LCX, Roche COBAS® Amplicor™, Roche Amplicor™, Bectin-Dickenson SDA, Johnson & Johnson PCR systems, and succeeding generations of such instruments. Alternatively, the inventive method and materials therefor can be designed to provide any suitable output volume of fluid that contains the prepared nucleic acid, such as, for example, from about 100 nl to about 750 $\mu$l, preferably from about 500 nl to about 500 $\mu$l, more preferably from about 1 $\mu$l to about 250 $\mu$l, more preferably yet from about 20 $\mu$l to about 200 $\mu$l, and most preferably from about 40 $\mu$l to about 150 $\mu$l. For example, the Roche COBAS® Amplicor™ automated system for the polymerase chain reaction amplification is optimally used for analysis of a nucleic acid sample volume of about 50 $\mu$l, whereas the Abbott LCX automated system for the ligase chain reaction amplification is optimally used for analysis of a nucleic acid sample volume of about 100 $\mu$l.

The inventive method is designed for the preparation of nucleic acid from any biological sample. A biological sample used in the context of the present invention is any material that contains nucleic acid, i.e., RNA or DNA. Such a sample can be an entire organism, such as an insect, or a number of organisms, such as in the analysis of bacteria or yeast; or the sample can be a portion of an organism, such as a tissue, body fluid, or excretion. Suitable tissues from which a nucleic acid composition can be obtained includes, but is not limited to, skin, bone, liver, brain, leaf, root, and the like; i.e., any tissue of a living or deceased organism. The tissue can be substantially uncontaminated with other tissues of the source organism, or it can be so contaminated, or even contaminated with tissues derived from different organisms. Preferably, one knows the source of the organism or organisms from which a particular biological sample is taken prior to subjecting it to the method of the present invention; however, such knowledge is not always available, as in the instance of forensic samples.

Biological samples can also be clinical samples or specimens. For example, one can seek evidence of a disease or condition caused by an exogenous source by testing the nucleic acid taken from a sample of a certain clinical specimen, such as urine, fecal matter, spinal fluid, sputum, blood or blood component, or any other suitable specimen, for the presence of a particular pathogen, for example, as evidenced by the identification in the preparation of characteristic nucleic acid sequences contained within such a pathogen. One can also test for the existence or propensity for certain inborn genetic diseases or conditions in an individual, such as, for example, Huntington's disease, Tay Sach's disease, and others, by testing for nucleic acid sequences characteristic of such genetic diseases or propensities in the nucleic acid isolated from suitable clinical samples, such as any cellular matter of the tested individual, with the caveat that cells having rearranged or detectably less DNA with respect to that of germ line stem cells, such as red blood and antibody-forming cells, alone may not be sufficient for such a test.

The nucleic acid isolated using the present method and materials therefor is any suitable nucleic acid, where the suitability is determined by the sort of test desired. For example, for testing for the presence of a certain pathogen in an individual, preferably one would test for an identifying nucleic acid sequence or sequences found in a DNA composition taken from a clinical sample where the known biology of the pathogen and host would suggest that the pathogen would be found if the tested individual were so infected. Alternatively, for testing whether a particular gene is being expressed in an individual, one can test for such expression by seeking evidence of an identifying nucleic acid sequence or sequences in an RNA composition taken from a tissue in which the underlying biology/pathology indicates that the expression should or should not be found, as appropriate to the condition or disease being tested. Depending on the gene whose expression is being monitored, the RNA composition can be further refined to include predominantly polyadenylated or non-polyadenylated RNA species using methods known in the art. Alternatively, or additionally, size classes of RNA species can be selected for in the context of the present invention as well.

Biological samples applied to the inventive method can be freshly taken from an individual or isolated from nature, or such samples can be stored using suitable conditions, such as on ice. For example, a sample of blood can be collected from an individual using standard means, such as a hypodermic needle placed into an individual's vein and connected to a standard evacuated tube, for example, to draw the blood from the individual into the tube. The blood can be used directly or stored on ice, preferably in the presence of an anti-coagulant, such as heparin, citrate, or EDTA. For longer storage, the samples are preferably frozen, freeze-dried, or applied to a suitable substrate and dried thereon for storage of, for example, DNA. Such a suitable substrate includes any absorbent paper, such as a Whatman filter paper, or a treated membrane material that releasably binds DNA. A preferred such membrane is included in a commercial product named IsoCode™ Stix (Schleicher & Schuell, Inc., Keene, N.H.), which, in addition to reversibly binding DNA, also irreversibly binds hemoglobin (an inhibitor of certain nucleic acid amplification methods). The substrate-bound nucleic acid can then be extracted from the substrate and purified in the same fashion as a fresh sample, in accordance with the present invention.

As noted above, the nucleic acid prepared using the present invention can thereafter be subjected to genetic analysis, which includes but is not limited to hybridization- or amplification-based tests. Such tests commonly utilize methods known as Southern blots, electrophoresis, radio- or enzyme-labelling, polymerase-based amplification, ligase-based amplification, chemical-based amplification, and the like, which can be performed manually using protocols well-known in the art (see Ausubel et al., supra); alternatively, at least some of these methods have been subjected to automation, or changed to allow for automation, such as procedures used in the context of the following machines: COBAS® Amplicor™ and Abbott LCX.

More particularly, the present invention relates to a device for nucleic acid extraction from one or more biological samples, preferably comprising a removable cassette that is insertable into a slot in the device. Preferably, the device includes slots for four different cassettes that can be run concurrently, serially, or in a staggered fashion. The device preferably includes a physical enclosure covering its enclosed mechanisms, which comprise the internal chemical, electromechanical, electrical, electronic, and computer assemblies, as well as a power supply. The device preferably is designed to operate up to an altitude of 3000 meters, at room temperature that can vary from about 15° C. to about 32° C., and at a relative humidity not to exceed about 80% at about 32° C. The device preferably includes an operator interface, which includes a suitable display of symbol- or language-based information, such as a liquid crystal display, and a keyboard for inputting information, which can be numeric, alphabetical, or alphanumeric. The device also preferably includes a bar-code scanner as well as software for processing such information. Further software that is preferably included with the device include instrument control software dedicated to the bar-code reader as already noted, the sample loader sequencer and sample transfer sequencer, the cassette assay sequencer, the batch transporter loader sequencer, calibration of fluid movement, and regulatory requirements satisfaction control. Software is also preferably included in the device for user help functions, manual sample identification input, and error handler, wherein any perturbations or other perceivable error events are recognized and stored for output with a final result report. Power source used for operating the inventive device is standard line voltage of 100 to 240 Volts, alternating current, at a frequency of 50 Hz to 60 Hz.

The user interface preferably provides information to the laboratory technician who is to use the device. The technician preferably will be notified by the user interface of any warnings, error conditions, instructions for operating the device, as well as instructions provided in response to inquiries presented by the technician. For example, a red light/green light signal can be employed to signal when the device is ready to be operated, such as, for example, leave to load more sample containers. Operator commands such as "READY FOR SAMPLE LOADING," "SAMPLE LOADER FULL," "LOAD CASSETTES," "REMOVE CASSETTES," "PUSH START BUTTON TO INITIATE BATCH SAMPLE PREPARATION," "INSERT NEW BATCH SAMPLE CARRIER," "REMOVE BATCH SAMPLE CARRIER" are preferably displayed by the user interface at suitable times in the operation of the device.

The controller of the operations of the device and thus of the contained cassette preferably is a microprocessor. However, it can also be a simpler device comprised of timers, switches, solenoids and the like. The important feature of a controller is that it directs the activation of the means for impelling a fluid from one fluid chamber to another, and opens or closes valves as appropriate, according to a pre-set or programmable schedule that results in the operation of a nucleic acid preparation protocol, such as the protocol outlined below.

The cassette used in the context of the present invention can be made of any suitable material having characteristics of sufficient moldability for forming the cassette, sufficient strength and resistance to chemical attack, and the like; for example, the cassette is preferably formed of a molded plastic, such as high density polyethylene, but other materials that are suitably resistant to the chemistries used in nucleic acid preparation, such as glass and silicon-based materials, can be used. Where the cassette is formed of plastic, it is preferably formed by a molding process that is used to form cavities and channels that will be sealed with upper and lower plastic films to form fluid chambers and fluid exchange channels. Fluid chambers include supply, reaction, and waste chambers, between which communication is established via the fluid exchange channels. Such cavities and channels are formed in suitable materials, such as glass and silicon materials, by chemical etching or laser ablation. Upper and lower films typically have a thickness of from about 0.3 mils to about 5 mils, preferably from about 1 mil to about 3 mils. For fluid chambers having a diameter of about 1 cm or more, the film thickness is more preferably about 2 mils. The reaction chamber, in which the reactions relating to the nucleic acid preparation take place, typically has a thickness, between the upper and lower films, of from about 0.1 mm to about 3 mm, preferably of from about 0.5 to about 1.0 mm, and an area, defined by the inner surface of the upper or lower films, of preferably from about 0.05 $cm^2$ to about 2 $cm^2$, more preferably from about 0.1 $cm^2$ to about 1 cm², yet more preferably about 0.5 cm². The dimensions of the reaction chamber are preferably sized small enough to permit rapid throughput of fluids so that the chemical conditions of the substrates having nucleic acid attached thereto (discussed further below) can be exchanged predictably and rapidly (on the order of about one to about 10 seconds).

Fluid exchange channels typically have a diameter between about 200 and about 500 µm. Supply chambers typically have a volume between about 5 and about 500 µl, preferably from about 10 to about 200 µl, more preferably from about 30 to about 160 µl. The supply chambers can contain reagents required in the preparation of the nucleic acid, such as lysis reagent, wash fluid, microparticles, Tris-EDTA (TE) buffer, and the like; such reagents can be contained in the supply chambers in dry or liquid form, and if in dry form, can be constituted with water contained in other supply chambers, or from water delivered from an external source. Metering chambers preferably have a volume between about 5 and about 50 µl. Preferably, the total volume of each reaction chamber is between about 5 µl and about 200 µl, more preferably, between about 10 µl and about 100 µl. Preferably, each reaction chamber has a thickness (i.e., distance between upper film and lower film) of about 1 mm or less.

The upper and lower films preferably are resistant to temperatures as high as about 120° C. and are between about 0.5 and about 4 mils in thickness, more preferably, between about 1 and about 3. The thinness of the membranes facilitates rapid heat exchange between the reaction chamber and an adjacent heating or cooling device, which can be used to establish a constant temperature for the nucleic acid preparation, if desired.

The cassette comprising the aforementioned fluid chambers, including supply, waste, and reaction chambers, fluid exchange channels, separable sample transfer/storage strip, and the valves and pumps further discussed hereinbelow, can have any suitable design. Indeed, any cassette design that includes at least one supply chamber, at least one reaction chamber, at least one waste chamber, at least one sample transfer/storage unit, and means of communication therebetween (i.e., the fluid exchange channels) suitable for the preparation of nucleic acid is preferred. More preferred, the cassette comprises up to six wells for entry of a sample container and its contents. Thus, the device that preferably has four slots for insertion of cassettes has the capacity to process up to 24 samples at a time.

The cassette is preferably encased or partially encased in a structure called a caddy, which is suitable for protecting the components of the cassette. The present device also comprises a means for moving the cassette from or into the caddy. Such means for separating the cassette from the caddy, and re-encasing the cassette in the caddy prior to removing the cassette from the device, include pneumatic hydraulic or electric motor-activated means; preferred means for separating and re-encasing the cassette in the caddy is electric motor-activated means.

Preferably, the cassette is a hollow body having a top side, an exterior, an interior, at least one slot for the placement of the cassette, and at least one well for the placement of a sample container. The sample container contains the biological sample that is subjected to the method of the present invention, the steps of which take place in the cassette. The resultant prepared nucleic acid is deposited into the aforementioned separable sample transfer/storage strip, where the extracted nucleic acid can be transferred or stored, each resultant sample separately from one another. For inserting the biological sample into the cassette, the cassette has suitable entry ports designed to accommodate sample containers formed of standard evacuated tubes in which certain biological samples are collected, or other suitable containers in which a biological sample can be contained. For example, as discussed above, a suitable sample can be applied to a solid substrate, such as a porous or adsorptive paper or a membrane having suitable reactive groups for binding RNA or DNA or both. Nucleic acid absorbed or adsorbed onto such a solid substrate can be stored in a wet or dried condition, under refrigerated (e.g., 4° C. or −20° C.) or ambient (i.e., about 25° C.) temperature conditions, and extracted into a suitable fluid (such as standard phosphate buffered saline or 1M Tris-EDTA buffer, pH 7–8 for application of the present method of nucleic acid preparation. Preferably, the cassette has more than one well; more preferably, the cassette has six wells.

In a preferred embodiment, the cassette has a movable input transfer sample bar. The movable input transfer sample bar has attached to it hollow needles (or cannulas) through which air or sample can flow into or from the sample container, respectively. The input transfer sample bar is positioned in an unengaged position such that the cannulas are not in communication with the sample container, or in an engaged position such that the cannulas are in communication with the sample container; the input transfer sample bar moves between these two positions as required by an operator of the device. Means for effecting the movement of the input transfer sample bar includes a pneumatic hydraulic device or an electric motor; preferred means for moving the sample transfer bar is an electric motor.

The device of the present invention further comprises an air nozzle which serves as a connector in communication with means for accessing, storing, or generating pressurized air. The air nozzle preferably is used in communication with the cannula that provides means for inserting air into the sample container, thereby providing means for increasing pressure that will force fluid in the sample container into the cassette. Means for accessing pressurized air includes, for example, suitable fittings for attachment of an air hose to a source of pressurized air. Means for storing pressurized air includes, for example, a vessel capable of holding air in excess of one atmosphere. Means for generating pressurized air includes, for example, an air compressor or the combination of chemicals that upon contact evolve gas.

The device of the present invention also comprises a means for sealing sample input channels of the cassette. Such means includes, for example, crimping of a rigid, meldable material, such as a metal, that is placed adjacent to the sample input channels; alternatively, such means can be the melting or fusing of the material of the cassette itself, wherein the cassette is composed of a fusable material. Such a material preferably fuses in response to heat, such as, for example, a localized elevation to 160° C. in the instance of using polyethylene as the material of the cassette walls, preferably high density polyethelene.

The device of the present invention further comprises valve actuators located in the interior of the device for opening and closing valves in the cassette. Such valve actuators preferably make direct contact with the cassette at the locations of valves contained within the cassette, which valves regulate the direction of flow of fluid within fluid exchange channels that also are located within the cassette. Similarly, the device also includes one or more pump actuators for moving fluid in or out of fluid chambers in the cassette. Such pump actuators preferably make direct contact with the cassette at the locations of pumps contained within the cassette, which pumps forceably move fluid through the fluid exchange channels and into or out of fluid chambers. Preferably, at least one of the pump actuators comprises a foot-pad pump with foot-pads designed to push on the supply chambers to open the sealed outlets and pump fluid into the fluid exchange channels.

The device of the present invention also comprises (1) a power supply, (2) a bar-code reading means, (3) a sensor means in the slot or well, (4) a memory means, and (5) a separating means for separating the strip from the remainder of the cassette. The power supply is any suitable power supply. The bar code reading means can be provided by any suitable bar code reading device, such as a hand-held wand or a built-in reader, such as the Opticon CCD Scanner. The sensor means for recognizing when a cassette is filling a slot or when a sample container is filling a well is, for example, a pressure-sensitive switch that completes an electric circuit when the slot or well is occupied, thereby providing a signal that can be interpreted by the processing means of the device, and registered in the memory means of the device. An alternative sensor means is photoelectric, wherein a light beam is disrupted upon insertion of a cassette or sample container. The memory means is any suitable memory means that uses analog or digital logic, which can be downloaded directly into a suitably programmed computer, and which can be accessed to print out a hard copy of the information stored therein. The separating means is preferably a knife having a heating means in communication thereto, the use of which seals both the strip and the remainder of the cassette.

One embodiment of the cassette used in the context of the present invention includes:

(1) one or more sample entry ports located on the input transfer sample bar that are serially and respectively in communication with the same number of wells of the device, wherein the ports are also in communication with input sample storage reservoirs of the cassette;

(2) one or more reaction flow-ways that are serially and respectively in communication via fluid exchange channels with the same number of sample input storage reservoirs;

(3) fluid chambers in communication with the fluid exchange channels, wherein fluid chambers are supply chambers for reagents, reservoirs for samples, or reaction chambers;

(4) valves for controlling the flow of fluids in the fluid exchange channels; and (5) a sample transfer/storage strip having at least one of the fluid chambers that is in communication with a reaction flow-way.

Such a cassette can include reaction flow-ways that are dedicated to controls for monitoring the effectiveness of the reactions designed into the cassette. For example, two reaction flow-ways can be dedicated to positive and negative control samples containing or not containing nucleic acid, respectively. The input transfer sample bar on the cassette comprises a first cannula that is an entry port and connects the sample container to the sample input channel and a second cannula that connects the same sample container to the air nozzle upon movement of the input transfer sample bar and engagement of same with the sample container. The supply chamber design used in this embodiment of the cassette is preferably that of a Bursapak™ supply chamber having a releasable seal blocking an outlet or outlets into the fluid exchange channels of the reaction flow-way. The Bursapak™ supply chamber is collapsible upon evacuation and fillable from a vacuum-collapsed state to a defined volume. Such supply chambers store and deliver to the reaction flow-way a lysis reagent, microparticles, wash fluid, or buffer alone. The DNA Direct™ system of Dynal (Lake Success, N.Y.) is a preferred system of lysis useful in the context of the present invention.

The microparticles used in the context of the device comprise a compound that binds specifically to nucleic acid or is paramagnetic, such as a paramagnetic bead. Paramagnetic beads useful for facilitating chemical processes conducted in a cassette are available from several sources, including Bang Laboratories (Carmel, Ind.) for beads lacking conjugated biomolecules, Dynal (Lake Success, N.Y.) for beads conjugated to various antibodies (for instance, antibodies that bind to the CD2 cell-surface receptor), and CPG (Lincoln Park, N.J.) for beads with a glass matrix and a variety of surface bonded organics. For applications where the beads will be washed into and out of reaction chambers, each bead will preferably have a diameter of less than about 1 mil, more preferably, less than about 0.5 mil, which diameter facilitates entry and exits through the channels by which material is inserted or evacuated from a reaction chamber.

Figure 2:
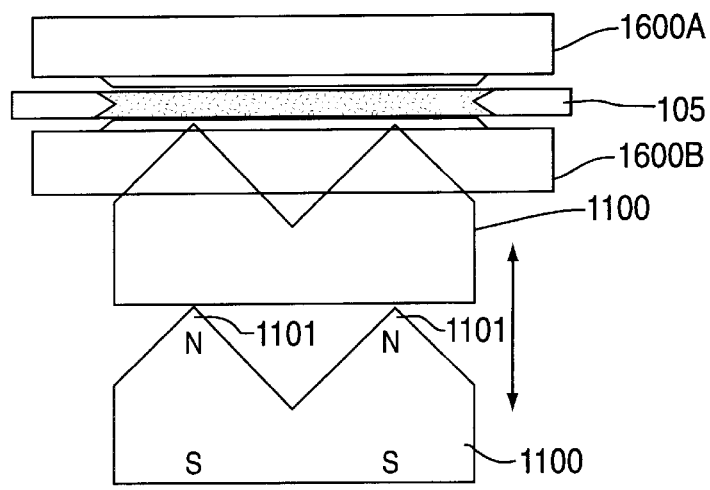
FIG. 2 shows an example of a magnet useful for locking paramagnetic beads at a certain location in a cassette.

In a preferred embodiment, the beads are locked in place in the reaction chamber or chambers using magnetic fields. To generate sufficient force upon the beads, the magnet used preferably generates a sufficient magnetic field gradient within a reaction chamber. Such magnets can be constructed by forming sharp edges on highly magnetic permanent magnets, such as those formed of rare earths, such as the neodymium-iron-boron class of permanent magnets. Such a permanent magnet is available from, for example, Edmund Scientific (Barrington, N.J.). Sharp edges of dimensions suitable for a particular reaction chamber are, for example, formed by abrasive grinding of the magnetic material. An example of such a shaped magnet 1100 is shown in FIG. 2, where the magnet has a roof-shape at one of the poles. The illustration shows a preferred embodiment where there are two roof shapes and illustrates that the magnet can be brought adjacent to or can be removed from a cassette. In the illustration, lower auxiliary block 1600B has slots (not visible) that allow the magnet 1100 to be placed adjacent to a cassette. This magnet suitably has dimensions such that the length of the peak of the roof-shape matches the cross-sectional size of a reaction chamber. To maximize the field gradient acting on the paramagnetic beads, the peak 1101 of the magnet 1100 is preferably placed adjacent to the reaction chamber or other structure in which the beads are located. The paramagnetic beads are held in place by leaving the peak 1101 adjacent to the beads. Another way in which high magnetic field gradients can be achieved is to make uniform slices of a magnetic material and use an adhesive to join the slices in alternating N to S orientations. Such alternating slice magnets have high magnetic field gradients at the junctions of the slices.

The sharp-edged magnets described above are effective in adhering the paramagnetic beads in one place and in moving beads located, for instance, in a fluid exchange channel or in a reaction chamber, from one location to another. Such magnets thus can help retain the paramagnetic beads in one place, for instance when a fluid in a reaction chamber is being removed from that chamber but it is desirable to leave the beads in the chamber. Magnets with locations having high magnetic field gradients that are particularly suitable for use in this context are described in U.S. Provisional Patent Application No. 60/006,202, filed Nov. 3, 1995, titled "Magnet," Docket No. DSRC 11904P now U.S. Ser. No. 08/742,971, which is incorporated herein in its entirety by reference.

Various cell binding beads (e.g., beads having bound antibodies specific for a certain subset of cells) can be used to adhere selected cells from a population of cells. The beads can be locked in place magnetically, for instance, if the beads are paramagnetic, while non-adherent cells and fluids are washed away. Thus, cell-binding beads can be used to concentrate small sub-populations of cells. Thus, the present invention of preparing nucleic acid from a biological sample in another preferred embodiment isolates a particular cell type from the sample prior to extracting the nucleic acid therefrom.

Figure 3A:
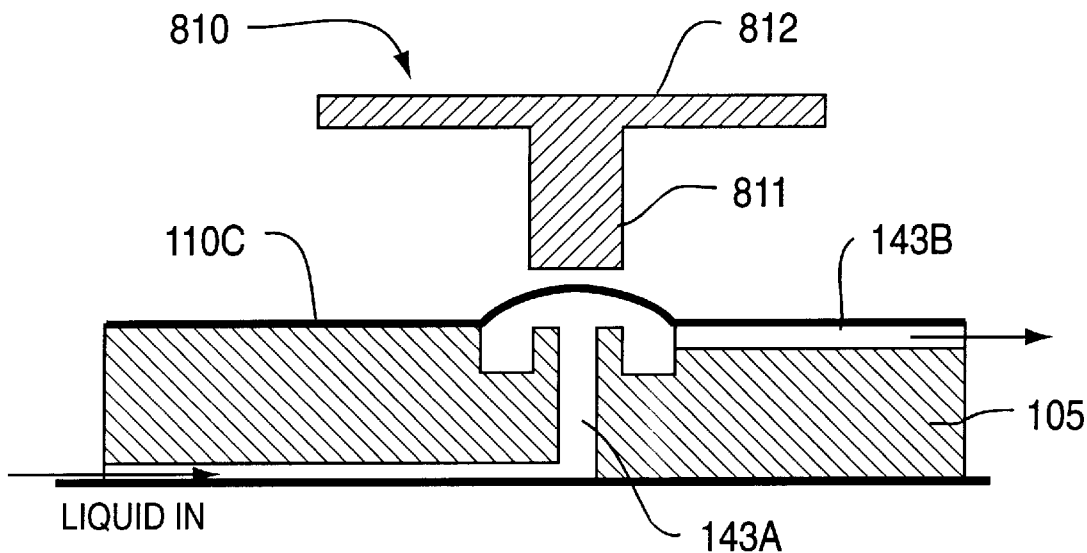
FIG. 3A and 3B show a plunger-type valve mechanism for regulating fluid flow through a cassette.
Figure 3B:
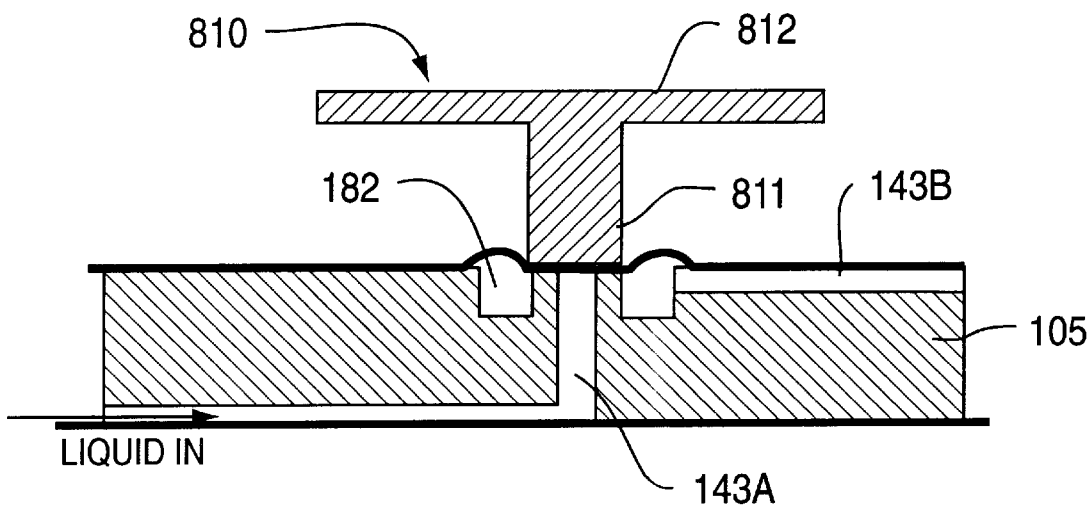
Figure 5:
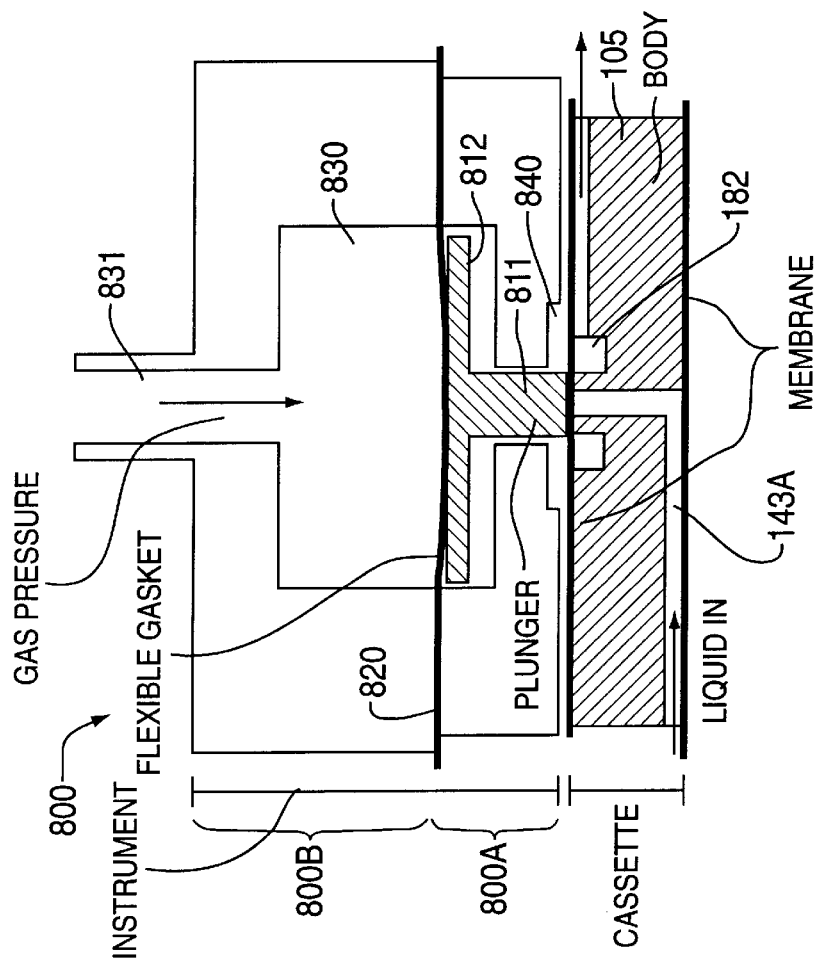
FIG. 5 shows the parts of a plunger-type valve located outside the cassette (i.e., in the instrument).
Figure 4:
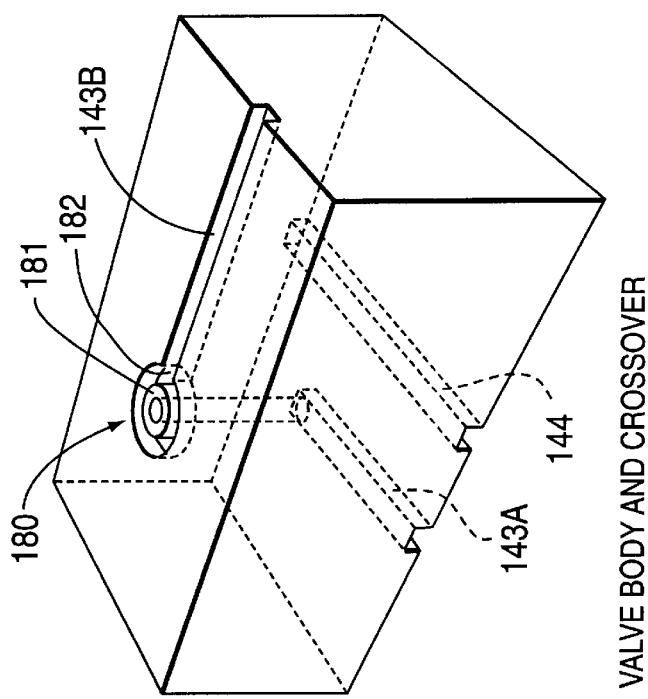
FIG. 4 shows in perspective view the part of a plunger-type valve located in the body of a cassette.

The cassette used in the context of the present invention includes, inter alia, valves that allow the device to direct flow of fluid in the fluid exchange channels between fluid chambers. FIGS. 3A, 3B, 4 and 5 illustrate one embodiment of the invention that utilizes plunger-type valves to control the flow of fluids in a cassette. The operation of such a plunger-type valve in a cassette is illustrated with reference to FIGS. 3A and 3B, although plunger-type valves should in no way be viewed as limited to this embodiment, which is being referred to here simply to illustrate the operation of this variety of valve. Plunger 810 has a plunger rod 811 and a piston 812. In the position illustrated in FIG. 3A, plunger rod 811 is withdrawn away from such that third film 110C, which is embossed to protrude away from the seat 181 of valve 180, does not interfere with fluid flow from alpha third fluid exchange channel 143A, into valve 180, and out through beta third fluid exchange channel 143B. In FIG. 3B, plunger rod 811 presses film 110C against valve seat 181, blocking fluid flow. FIG. 5 shows a three-dimensional view of valve 180, including valve seat 181 and valve trough 182.

The plunger 810 can be constructed of numerous durable materials including without limitation a plastic such as polycarbonate or metal such as stainless steel or aluminum or the like. The diameter of plunger rod 811 is typically from about 20 to about 100 $\mu$m, preferably about 60 $\mu$m, while piston 812 typically has a diameter from about 100 to about 300 $\mu$m, preferably about 200 $\mu$m. Preferably, the ratio of the cross-sectional area of the piston 812 to that of the plunger rod 811 is at least about 10-fold, thereby providing a corresponding mechanical advantage.

A pneumatic mechanism for operating plunger 810 is illustrated in FIG. 5. A device of the present invention can have a pneumatic device 800 formed of first portion 800A and second portion 800B, which can be joined together, for instance, by bolts, rivets, adhesives or snap-fitting pieces. Interposed between the first and second portions 800A and 800B is flexible gasket 820, which can be formed of a suitable film such as poly (2-chloro-1,3-butadiene) (e.g., Neoprene, DuPont de Nemours, Wilmington, Del.) or silicon rubber. Flexible gasket 820 can be held in place by the clamping action of first and second portions 800A and 800B, which adherent force can be supplemented using heat sealing or adhesive. Pneumatic cavity 830 is formed in both first and second portions 800A and 800B and has a cavity inlet 831. Fluid, preferably a gas, is inserted through cavity inlet 831 to pressurize the part of pneumatic cavity 830 located above the gasket 820 and cause the gasket 820 to press against plunger 810, causing plunger 810 to press against valve seat 181. In the absence of such fluid pressure in pneumatic cavity 830, pump induced pressure in third fluid exchange channel 143A is sufficient to displace (a) third upper cover into displacement cavity 840 and (b) plunger 810 from the valve seat 181, thereby allowing flow. Pneumatic device 800 can be formed of numerous durable materials including without limitation a plastic such as polycarbonate or metal such as brass or aluminum or the like.

The present invention also relates to a method for extracting nucleic acid from a biological sample using the device described hereinabove. In this method, the inventive device for nucleic acid extraction from one or more biological samples is provided the samples are extracted via the cassette. As discussed above, the cassette can be inserted into a protective caddy, at least one of which is preferably placed into a slot on the inventive device. One or more sample containers are preferably inserted into wells on the cassette, each such container containing a biological sample for extraction. As appropriate, air pressure is applied by way of the second cannula located on the aforementioned input transfer sample bar to expel the biological sample from the sample container, whereupon the sample enters the cassette via sample input valves thereby filling the input sample reservoirs of the cassette. The resultant nucleic acid preparation can be delivered in any suitable volume, as discussed above, and is preferably delivered in volumes that range, for example, from about 20 $\mu$l to about 200 $\mu$l, contained in the sample storage/transfer strip.

The method for nucleic acid preparation preferably further comprises inclusion of control biological samples, wherein a positive control including nucleic acid and a negative control including no nucleic acid are included. Internal controls are also contemplated to be used in the context of the present invention, wherein a known segment of nucleic acid, such as a plasmid or portion thereof having appropriate initiation sites for transcription, for example, is added to a biological sample to be subjected to preparation of its contained nucleic acid by the inventive device. Thus, efficiencies of the nucleic acid preparation method can be gauged, for example, by testing for activity with respect to the added internal control nucleic acid. The biological sample subjected to the inventive method is any suitable sample that may contain nucleic acid; preferably, the biological sample is selected from the group consisting of whole blood, plasma, serum, urine, and suspensions of swab or sputum.

The inventive method preferably includes steps for extracting the nucleic acid from the biological sample, such as:

(1) lysing of cells included in the biological sample in the presence of a surface having specific affinity for nucleic acid; and (2) substantially purifying the nucleic acid from the lysed biological sample.

The surface used in the context of the present method is a microparticle that has specific affinity for nucleic acid or is paramagnetic, as discussed above. The lysis reagent used in the context of the present invention preferably is combined with the microparticles, such as those included with the Dynal DNA Direct™ system.

The method further includes recordation of dynamic data entries, dynamic process parameters, results, error information, location of well into which a given sample container was inserted, location of slot into which a given cassette was inserted, and correlating such records to a bar-code identifier associated with a sample, all of which are captured and stored by the memory means.

The cassette used in the context of the present device and method of use thereof can enclose the requisite chemistries for nucleic acid preparation as a sealed or unsealed unit. Preferably, the cassette of the present invention is a sealed-chemistry cassette. The cassette preferably includes a separable sample transfer/storage strip and a movable input transfer sample bar, as fully disclosed hereinabove. In a preferred embodiment, the cassette preferably further comprises:

(1) one or more sample entry ports, more preferably two or more sample entry ports, located on the input transfer sample bar that are serially and respectively in communication with the same number of input sample metering chambers located in the cassette;

(2) one or more reaction flow-ways, more preferably two or more reaction flow-ways, that are serially and respectively in communication via fluid exchange channels with the same number of sample input metering chambers;

(3) fluid chambers in communication with the fluid exchange channels, wherein fluid chambers are supply chambers for reagents, metering chambers for samples, or reaction chambers, and wherein the supply chambers store and deliver to the reaction flow-way a lysis reagent, microparticles in a buffer, or buffer alone for nucleic acid extraction; and (4) valves for controlling the flow of fluids in the fluid exchange channels;

wherein the sample transfer/storage strip includes at least one of the fluid chambers that is in communication with the reaction flow-way. The input transfer sample bar comprises a first cannula that is an entry port and connects the sample container to the sample input channel and a second cannula that connects the same sample container to the air nozzle upon activation of the input transfer sample bar and engagement of same with the sample container.

The cassette of the present invention preferably includes a supply chamber having a releasable seal blocking an outlet or outlets into the fluid exchange channels of the reaction flow-ways. One such supply chamber is a Bursapak™ supply chamber. Each of the supply chambers is preferably collapsible upon evacuation and fillable from a vacuum-collapsed state to a defined volume.

The cassette of the present invention also preferably includes at least one transfer/storage strip releasably attached to the cassette, where the nucleic acid that is extracted from each sample is stored and transferred separately from one another. The separable transfer/storage strip is connected to the remainder of the cassette in a manner by which, upon being separated, both the strip and the remainder of the cassette is sealed. This simultaneous sealing is preferably effected by use of heat or mechanical crimping and, respectively, fusable or meldable material at the junction between the storage/transfer strip and the remainder of the cassette.

The following examples further illustrate the present invention but, of course, should not be construed as in any way limiting its scope.

EXAMPLE 1

This example illustrates features of a cassette constructed in accordance with the present invention.

Figure 6:
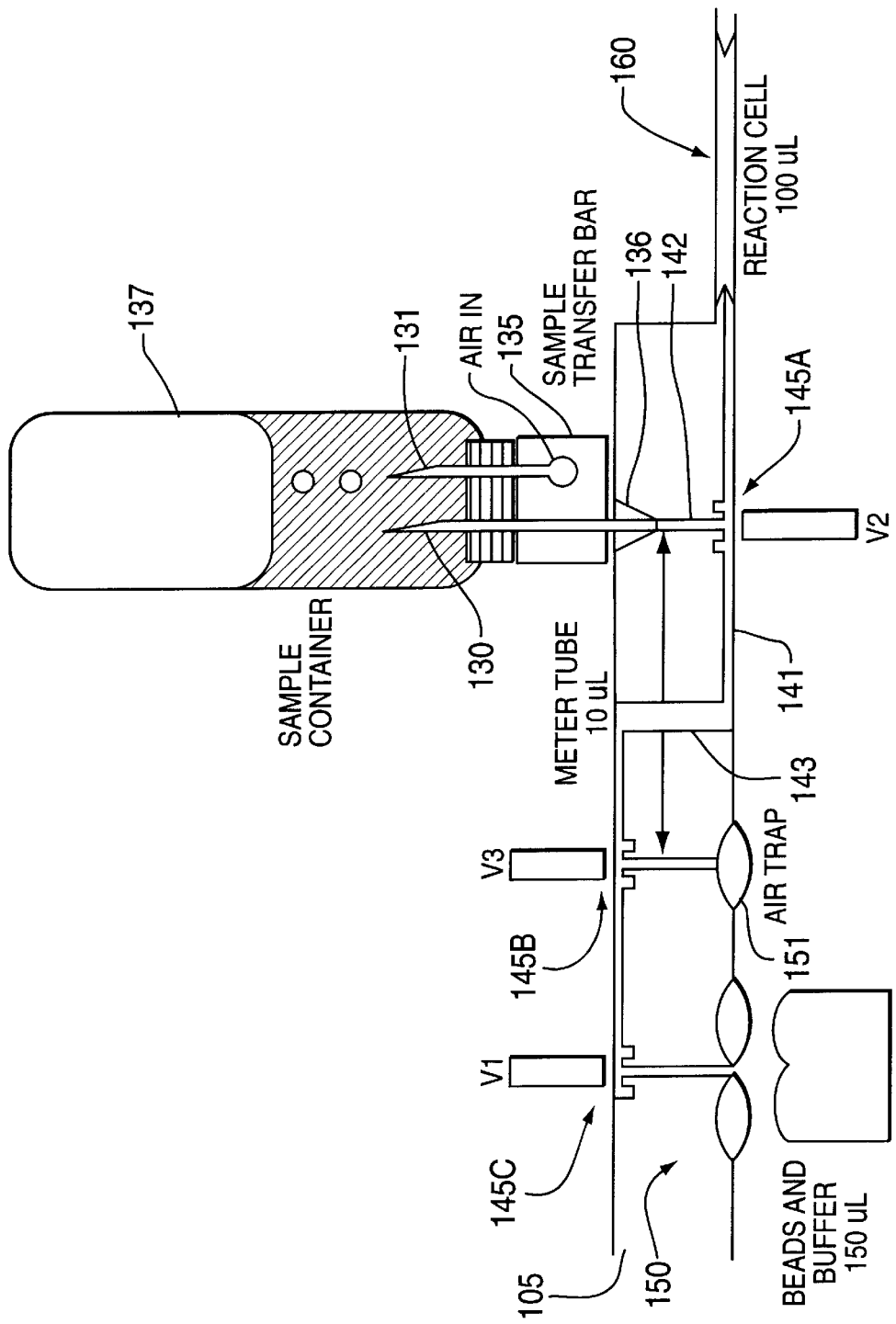
FIG. 6 shows a cross-sectional view of certain features of a cassette of the invention.

FIG. 6 shows a cross-sectional view of a portion of a cassette 100 constructed according to the invention, wherein reagent such as a reagent containing suspended beads, for example, and sample can be introduced into the cassette. The cassette. 100 has a body 105 in which are defined sample inlet channel 142, inlet 136, first fluid exchange channel 141, alpha valve 145A, beta valve 145B, gamma valve 145C, reagent supply chamber 150, reaction chamber 160 and air trap 151. First fluid exchange channel 141 incorporates metering tube 143. Assuming reagent supply chamber 150 contains beads, sample introduction is conducted as follows. Sample transfer bar 135, which has inlet cannula 130 and gas-flow cannula 131 is inserted into the inlet 136 so that the inlet cannula 130 and inlet 136 form a seal. Alpha valve 145A is closed. Sealed sample container 137 is attached to the sample transfer bar 135 so that the inlet cannula 130 and gas-flow cannula 131 both pierce the seal of sample container 137. A foot-pad pump is operated to keep air trap 151 closed and empty (it is illustrated as filled). All three illustrated valves are opened and a foot-pad pump is operated to push the reagent in reagent supply chamber 150 into reaction chamber 160. Foot-pad pumps at reaction chamber 150 then reverse the flow. This process is repeated as need to suspend the beads. After one or more cycles of this process, the reagent is locked in reagent supply chamber 150 by closing gamma valve 145C. With beta valve 145B open, gas is introduced through gas-flow cannula to force sample into inlet channel 142 and metering tube 143. Excess sample volume and air that was trapped in the inlet cannula 130 or inlet channel 142 is pushed into and fills air trap 151. Next a foot-pad pump is operated to push the reagent with suspended beads and the metered sample into reaction chamber 160.

EXAMPLE 2

This example illustrates the Bursapak™ fluid chamber, which is used in one embodiment of the present inventive device to meter sample and store reagent and wash fluids.

Figure 8A:
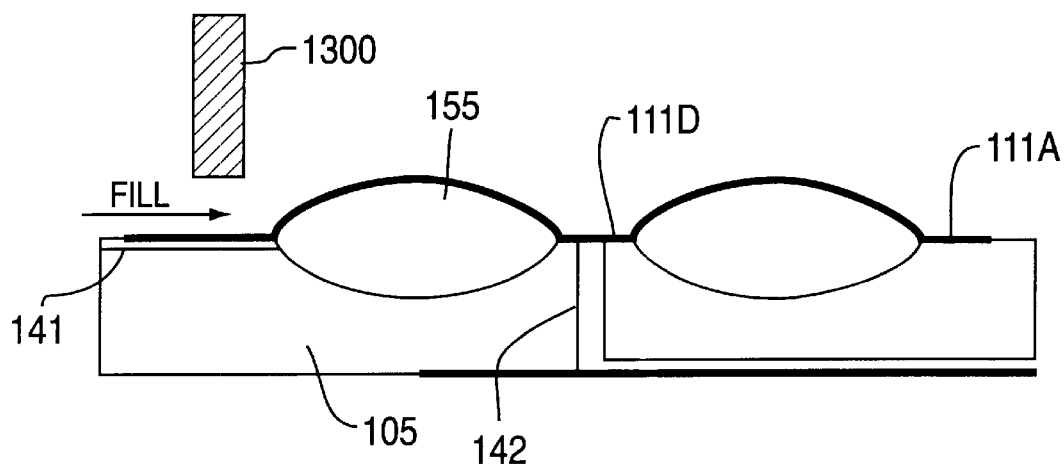
FIG. 8A shows a side view of a supply chamber.
Figure 8B:
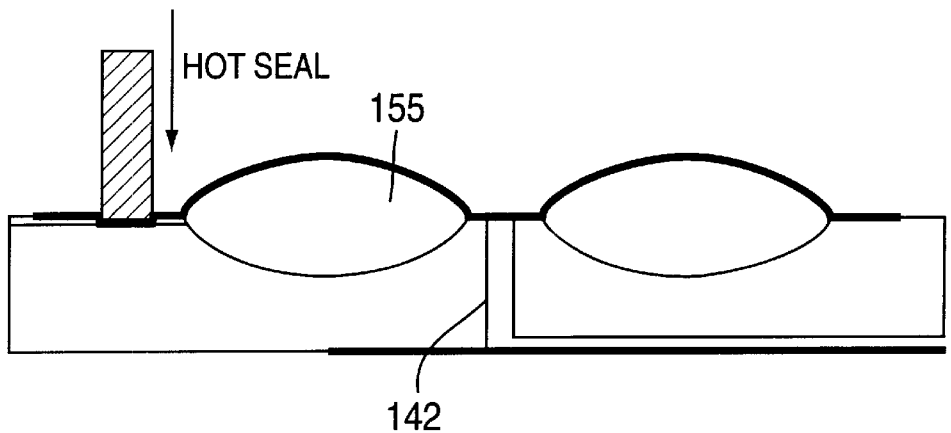
FIG. 8B illustrates a method for sealing closed a fluid exchange channel.
Figure 8C:
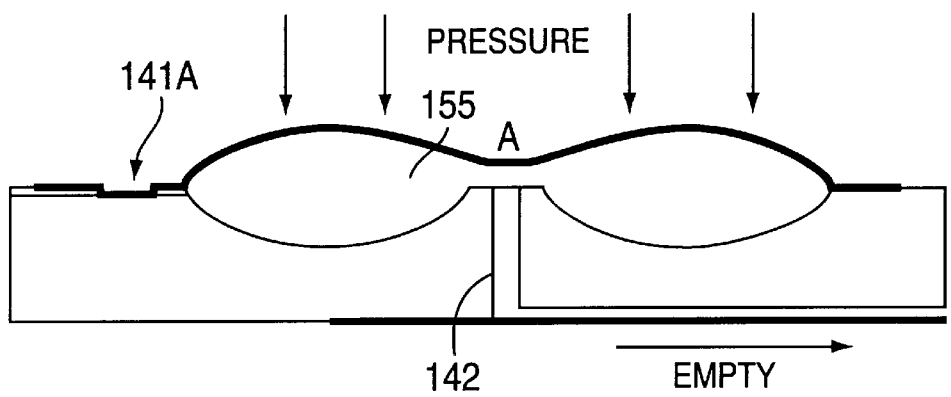
FIG. 8C illustrates how pressure can be used to open a Bursapak supply chamber.
Figure 8D:
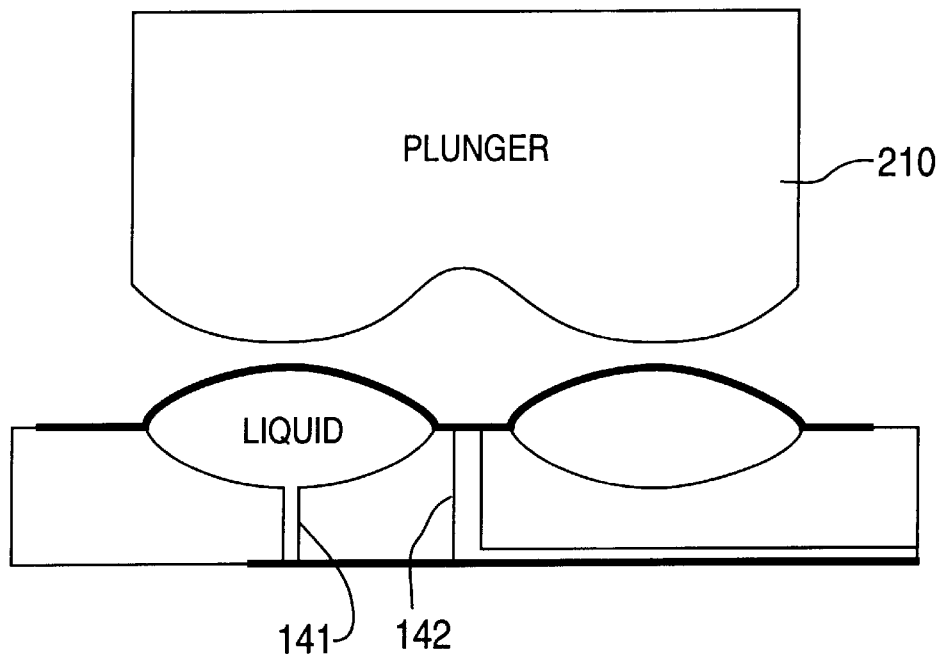
FIGS. 8D and 8E illustrate a foot-pad that can be used to pressurize the fluid in a supply chamber.
Figure 8E:
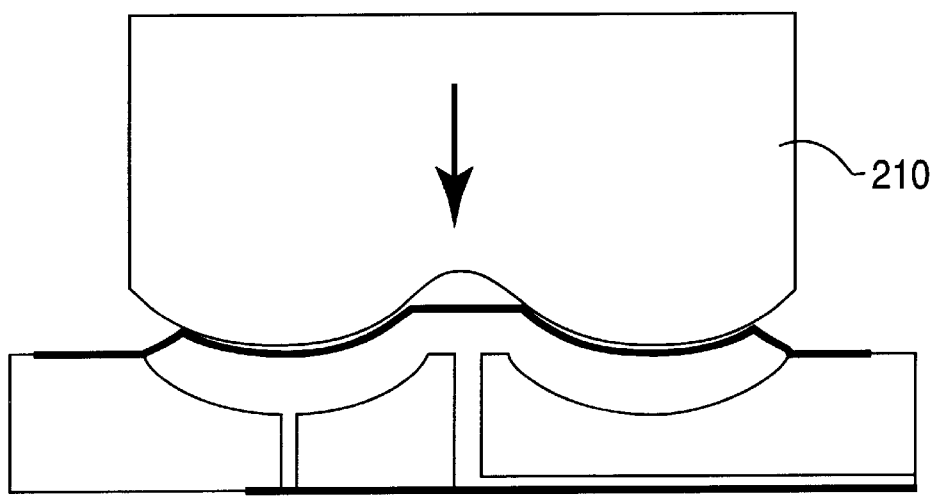

FIG. 8A shows a side view of a Bursapak™ sample storage reservoir 150 having cavity 155, into which sample is inserted. The Bursapak™ sample storage reservoir 150 has an inlet first fluid exchange channel 141, which is preferably sealed, for instance by heat sealing at sealing location 141A, after the Bursapak™ sample storage reservoir 150 has been filled with fluid sample, and an outlet second fluid exchange channel 142 which is initially sealed with a fourth seal portion 111D of first upper film 110A. In certain embodiments, seal portion 111D is sealed with a weaker adhesive or lower temperature sealing die than are the other seals of the Bursapak™ chamber. FIG. 8B shows the use of die 1300 to heat seal first fluid exchange channel 141, at sealing location 141A. FIG. 8C illustrates how pressure—indicated by the arrows—applied to the fluid in Bursapak™ sample storage reservoir 150 is effective to pull the seal portion 111 away from the outlet second fluid exchange channel 142. FIG. 8D illustrates a foot-pad 210 that is used to apply pressure to the fluid in Bursapak™ sample storage reservoir 150 and pump it through outlet second fluid exchange channel 142. Foot-pads are fabricated of any suitably sturdy material including, without limitation, aluminum, plastics, alumina, copper, sintered beryllia, and the like. Upper films 110 and lower films 120 are preferably constructed of a flexible film such as a polyethylene, polyvinylidene fluoride or polyethylene/polyethylene terephthalate bi-layer film. Suitable films are available from Kapak Corporation, Minneapolis, Minn. or E. I. duPont de Nemours and Co., Wilmington, Del. Polyethylene/polyethylene-terephthalate bi-layer film such as 3M No. 5 or 3M No. 48 (3M Corp., Minn.) or Dupont M30 (DuPont de Nemours, Wilmington, Del.) are particularly preferred. The polyethylene layer is preferably positioned against body 105. FIG. 8E shows the foot-pad used to pump fluid out of Bursapak™ sample storage reservoir 150 in its fullest engaged position.

The first upper film 110A is embossed or shaped, for instance by applying suitably shaped, heated dies to the first upper film 110A, so that it can protrude away from the body 105 when the sample storage reservoir 150 is filled and will rest, without substantial stretching, against the bottom of sample storage reservoir 150 when the sample storage reservoir 150 is evacuated.

EXAMPLE 3

This example illustrates a six-channel cassette constructed in accordance with the present invention.

Figure 9:
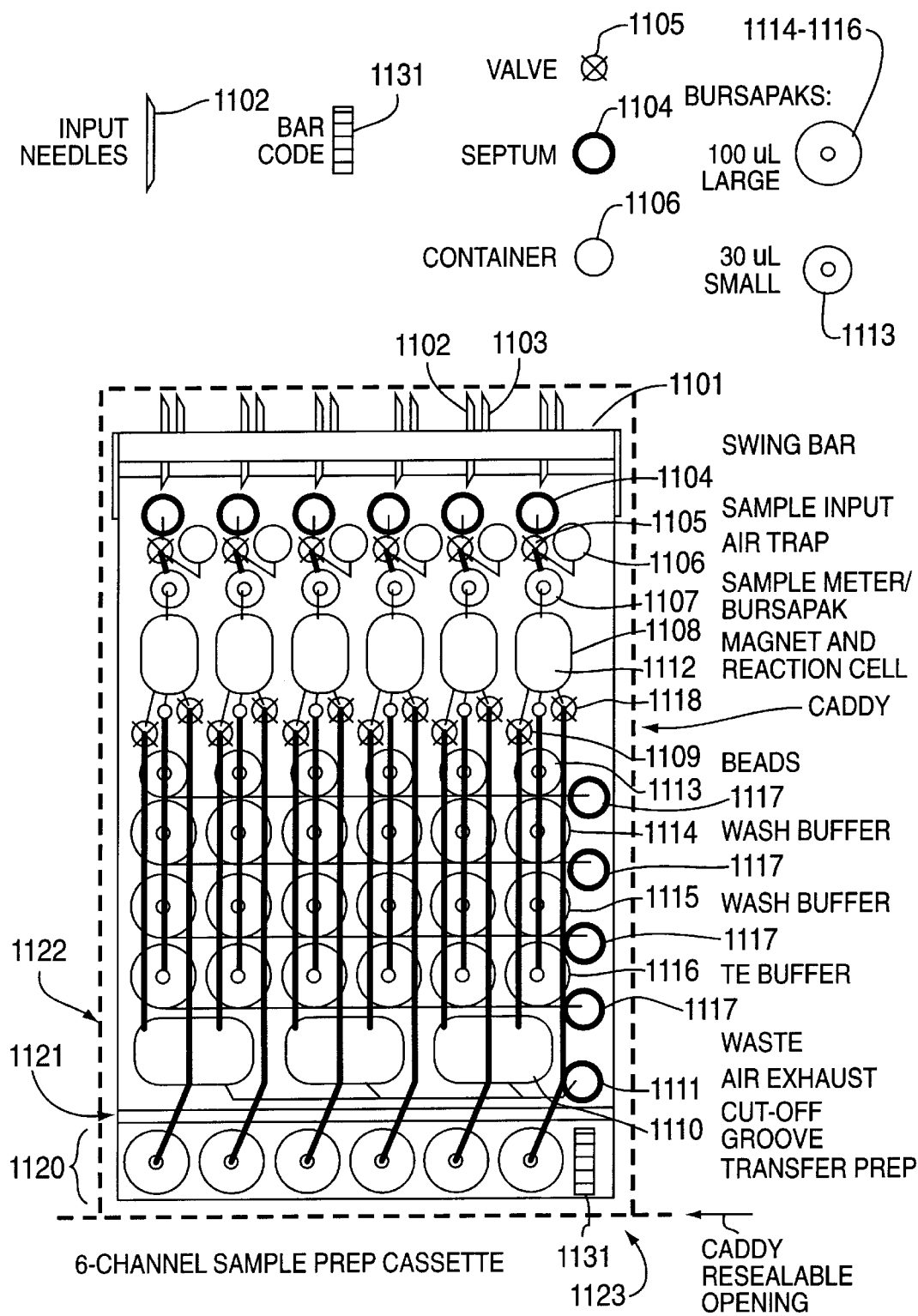
FIG. 9 is a diagram representing one embodiment of the cassette of the present invention.

A cassette is illustrated in FIG. 9, which is designed in accordance with the present invention. The illustrated cassette has planar dimensions of 4 inches by 6 inches, and is 0.2 inches thick, although other sizes are contemplated, including for instance in circumstances where the sizes of the fluid chambers and other components of the cassette differ from those illustrated. In this illustration, the solid lines connecting inlets, valves or fluid chambers represent fluid exchange channels. Those fluid exchange channels represented by dark lines are formed in the upper surface of the cassette body, while those represented by lighter lines are formed in the lower surface of the cassette body. At the top of FIG. 9 are illustrated the symbols used to represent an inlet cannula or needle 1102, a bar code 1131, a valve 1105, a septum or port 1104, a receptacle 1106, and Bursapak™ fluid chambers 1113–1116 of various sizes (sizes recited for illustrative purposes only).

FIG. 9 illustrates a cassette having six flow-ways for preparing up to six different biological samples, or a lesser number of samples thus leaving room for positive or negative controls, one set of such are run with each set of parallel nucleic acid preparations. The components for each flow-way are identical, albeit waste receptacles and air exhausts are shared as illustrated. The components of the rightmost flow-way illustrated in FIG. 9 are: input transfer sample bar 1101, sample input cannula or needle 1102, an air inlet cannula or needle 1103, a septum or port of entry for the sample 1104, a first valve 1105, an air trap receptacle 1106, a sample meter Bursapak™ 1107, a reaction chamber/magnet site 1108, a second valve 1109 connecting to a waste receptacle 1110, which is shared with the reaction flow-way that is second from the right, and which is serially connected to an air exhaust septum 1111 that is shared by all waste receptacles of the cassette. Further components of the rightmost flow-way include a burstable seal 1112 (part of a Bursapak™ design, for example) that serially connects the reaction chamber to other fluid chambers containing beads or microparticles 1113, a first wash buffer 1114, a second wash buffer 1115, and a standard Tris-EDTA (TE) buffer 1116 used in nucleic acid preparations. Air exhaust septa 1117 are serially connected to the respective fluid chambers of each flow-way, one air exhaust septum per set. A third valve 1118 regulates the connection between the reaction chamber/magnet site 1108 and the receiving fluid chamber 1119 included on the separable storage/transfer strip 1120 having a cut-off groove 1121. In the exemplified embodiment, the entire cassette is housed in a caddy 1122, which has a resealable opening 1123.

EXAMPLE 4

This example illustrates operation of the cassette illustrated in Example 3.

This discussion of operational features of the cassette structure shown in FIG. 9 assumes that the supply chambers of that structure are Bursapak™ design supply chambers. Up to six samples, or an equivalent number fewer if flow-ways are taken up by positive or negative controls, are loaded from a sample container by way of the sample input cannula 1102 that is part of the input transfer sample bar 1101. The device in a part not shown in FIG. 9 includes a pressurized air source that is connected to the air inlet cannula 1103 that is inserted into the sample container; input of pressurized air into the sample container forces the sample out of the sample container into the cassette at the input port 1104. The first valve 1105 is opened by the device, air bubbles are trapped in the air trap 1106, and the sample meter Bursapak™ 1107 is filled to capacity, which is 30 $\mu$l. After the sample meter Bursapak™ 1107 is filled, the fluid exchange channel at the point or near to the first valve 1105 is heat sealed by the device, thus closing the cassette to any possibility of contamination.

The reaction chamber/magnet site 1108 already would receive paramagnetic beads of 2.8 $\mu$m diameter that has specific and releasable affinity for nucleic acid prior to the adding of sample thereto. A foot-pad pump operates to propel in parallel the fluid and suspended beads from the bead-containing fluid chamber 1113 to the connected reaction chamber 1108. The bead-containing fluid chamber contains a volume of up to 30 $\mu$l. To assure that the beads are suspended, the foot-pad pump operating on the first supply chamber 1113 and foot-pad pump operating on the reaction chamber 1108 can alternately be operated to move the fluid back and forth between the first fluid chamber 1113 and reaction chamber 1108, thereby agitating the fluid and re-suspending the beads. Once the beads are sufficiently suspended, the contents of the sample meter Bursapak™ 1107 is caused to flow into the reaction chamber/magnet site 1108 by action of another foot-pad pump.

The second fluid chamber 1114 contains up to 100 $\mu$l of a lysis reagent that includes microbial, used in the DNA Direct™ system (Dynal Corporation). The third fluid chamber 1115 contains from about 100 $\mu$l of a wash fluid and the fourth fluid chamber 1116 contains from about up to 100 $\mu$l to about 5 ml of TE buffer.

A desirable feature for a cassette such as that illustrated in FIG. 9 is the ability to incorporate a positive control in one or more, but not all, of the reaction flow-ways. Thus, a material that should generate a positive nucleic acid preparation result can be inserted into a sample inlet port that otherwise may or may not produce a positive result (i.e., unknown biological samples) or in samples that should not produce a positive result (i.e., negative controls). In this way, the source of substances that interfere with the preparation can be determined. Any failure of the reaction flow-ways containing a positive control to generate a positive result or an appropriately strong positive result would indicate that a standard solution used in the assay contains a substance or has a property that interferes with the assay. Fluids expected to generate negative signals can also be incorporated into the cassette.

Not all fluid chambers 1113–1116 must be utilized. A supply chamber is avoided simply by not pumping its contents into the connected reaction chamber.

It is desirable to contain all waste fluids in the cassette 1101. Thus, the illustrated cassette 1101 has a waste receptacle 1110 of sufficient volume to accommodate all the fluids introduced into the cassette for at least up to two flow-ways. Waste receptacle 1110 is prepared in an evacuated state such that the films forming the outer wall of the waste receptacle 1110 rest against the inner surfaces of the waste receptacle 1110. As fluid is pumped into the waste receptacle 1110, the film will flex outwardly to provide room for the inserted fluid. It is desirable to confine the fluids to the cassette for instance to isolate biohazards and minimize cross-contamination between samples.

Fluid chambers 1113–1116 are also evacuated in like manner prior to filling. Most fluid chambers 1113–1116 will, in a preferred embodiment, be pre-filled prior to shipment to the laboratory where the nucleic acid preparations will be conducted.

Foot-pad pumps that operate to drain a fluid chamber 1113–1116 can remain engaged with the fluid chamber 1113–1116 to prevent back-flow into the respective fluid chamber 1113–1116.

EXAMPLE 5

This example illustrates the reproducibility of the use of microparticles for isolating DNA from a biological sample.

Twelve biological samples were processed for isolating DNA contained therein, using the following procedure. To 10 μl of whole blood, 100 μl of resuspended Dynabeads DNA DIRECT™ (Dynal Corporation; product no. 630.02) were added in a single, rapid pipetting action. This mixture was incubated at room temperature (about 25° C.) for 5 minutes. The DNA/Dynabeads complex was separated from the DNA Direct™ reagents by placing the tube in a magnetic particle concentrator (MPC) for 90 seconds and aspirating the supernatant. The complex was then subjected to four times of washing with 100 μl of washing buffer and resuspended in 30μl of TE by repeated pipetting. The DNA was eluted from the Dynabeads by incubating at 65° C. for 5 minutes and transferring the supernatant to a clean tube. 10 μl of the eluted DNA was then used in a standard β-Globin PCR assay. The resulting amplicon was analyzed on an 8% acrylamide gel, stained with SYBR Green, and the bands corresponding to the amplicon were qualified using a Molecular Dynamics phosphorimager system (Storm 840). The results were as follows:

| sample number | relative amplicon concentration |
| --- | --- |
| 1 | 370245.6 |
| 2 | 349973.9 |
| 3 | 310896.7 |
| 4 | 435869.3 |
| 5 | 401276.7 |
| 6 | 434117.1 |
| 7 | 285654.2 |
| 8 | 418048.2 |
| 9 | 358373.2 |
| 10 | 294655.6 |
| 11 | 305085.4 |
| 12 | 251965.4 |
| MEAN | 351346.8 |
| S. D. | 62178.52 |
| C. V. | 0.176972 |

The results were highly reproducible, having a coefficient of variation (C.V.) for 12 independent sample isolations of just under 18%. Accordingly, the Dynabeads DNA DIRECT™ system can be relied on in the microfluidic system based on these manual results.

While this invention has been described with an emphasis upon a preferred embodiment, it will be obvious to those of ordinary skill in the art that variations in the preferred device and method of use may be used and that it is intended that the invention may be practiced otherwise than as specifically described herein. Accordingly, this invention includes all modifications encompassed within the spirit and scope of the invention as defined by the following claims.

What is claimed:

1. A device for nucleic acid extraction from one or more biological samples, comprising a housing having a slot and a removable chemistry cassette, wherein the cassette fits into the slot, wherein the cassette has attached thereto a separable sample transfer/storage strip for holding and storing nucleic acids extracted from a biological sample, and wherein the cassette includes reagents suitable for nucleic acid extraction.

2. The device of claim 1, wherein the cassette is a sealed-chemistry cassette.

3. The device of claim 2, wherein the cassette has a movable input transfer sample bar attached to the cassette, wherein the input transfer sample bar comprises one or more sets of a sample entry port and a second cannula.

4. The device of claim 3, wherein the input transfer sample bar comprises the sample entry ports, which are first cannulas, and the second cannulas, wherein the first cannulas are for introducing a biological sample from sample containers into the cassette and the second cannulas are for introducing gas into sample containers.

5. The device of claim 4, wherein the cassette is encased in a caddy.

6. The device of claim 4, wherein the cassette comprises a hollow body having a top side, an exterior, and an interior.

7. A method for extracting nucleic acid from a biological sample using the device of claim 6, comprising:
(1) providing the device of claim 6 for nucleic acid extraction from one or more biological samples,
(2) inserting at least one caddy-encased cassette into the slot on the device, and
(3) extracting nucleic acid from a biological sample via the cassette.

8. The method of claim 7, further comprising connecting at least one sample container containing a biological sample for extraction to the input transfer sample bar wherein the biological sample is introduced into the device via the cassette.

9. The device of claim 6, further comprising a means for moving the cassette from or into the caddy.

10. The device of claim 9, further comprising a means for moving the input transfer sample bar.

11. The device of claim 10, further comprising a connector in communication with means for accessing, storing, or generating pressurized gas, wherein the connector is releasably attached to the second cannulas.

12. A method for extracting nucleic acid from a biological sample using the device of claim 11, comprising:
(1) providing the device of claim 11 for nucleic acid extraction from one or more biological samples,
(2) inserting at least one caddy-encased cassette into the slot on the device
(3) connecting at least one sample container containing a biological sample for extraction to the input transfer sample bar,
(4) adding gas to the at least one sample container by way of one of the second cannulas to expel the biological sample from the sample container, and
(5) extracting nucleic acid from the biological sample via the cassette.

13. The device of claim 11 wherein the cassette comprises at least one reaction flow-way and at least one sample input channel, wherein the at least one reaction flow-way is in fluid communication with the at least one sample input channel, which sample input channel is reversibly in fluid communication with one of the first cannulas on the movable input transfer sample bar, further comprising a means for sealing sample input channels, wherein each reaction flow-way comprises two or more serially connected fluid chambers.

14. The device of claim 13, wherein the at least one reaction flow-way further comprises an input sample reservoir, valves and valve actuators that allow or retard flow in the at least one reaction flow-way, wherein the valve actuators are located in the interior of the cassette for opening and closing valves in the cassette.

15. A method for extracting nucleic acid from a biological sample using the device of claim 14 comprising:
(1) providing the device of claim 14 for nucleic acid extraction from one or more biological samples,
(2) inserting at least one caddy-encased cassette into the slot on the device,
(3) connecting at least one sample container containing a biological sample for extraction to the input transfer sample bar,
(4) adding gas to the at least one sample container by way of a second cannula to expel the biological sample from the sample container,
(5) opening sample input valves thereby filling the input sample reservoir, and
(6) extracting nucleic acid from the biological sample via the cassette.

16. The method of claim 15, wherein the one or more biological samples include control biological samples, which include a positive control containing nucleic acid and a negative control not containing nucleic acid.

17. The method of claim 15, wherein the biological sample is selected from the group consisting of whole blood, plasma, serum, urine, and suspensions of swab or sputum.

18. The method of claim 17, wherein steps for extracting the nucleic acid from the biological sample after said sample has been introduced into the cassette comprise:
(1) lysing of cells included in the biological sample in the presence of a surface having specific affinity for nucleic acid; and
(2) substantially purifying the nucleic acid from the lysed biological sample.

19. The method of claim 18, further comprising delivering about 20 ml to about 200 ml of a substantially purified nucleic acid solution or substantially purified nucleic acid complexed to microparticles into the sample storage/transfer strip.

20. The method of claim 18, wherein the surface is a paramagnetic microparticle.

21. The device of claim 14 further comprising one or more pump actuators for moving fluid in or out of the fluid chambers.

22. The device of claim 21, further comprising a magnet that can be reversibly brought adjacent to the cassette.

23. The device of claim 22, further comprising a memory means.

24. The device of claim 23, wherein the memory means captures and stores data comprising dynamic data entries, dynamic process parameters, results, error information, location of the sample entry port and second cannula to which a given sample container is connected, or location of the slot into which a given cassette is inserted.

25. The device of claim 24, wherein two or more sample containers, each containing a biological sample, are each connected to separate sample entry ports.

26. The device of claim 25, wherein the biological samples are extracted in parallel.

27. The device of claim 24, wherein the memory means correlates the data to a bar-code indentifier associated with a sample.

28. The device of claim 23, further comprising a separating means for separating the sample transfer/storage strip from the remainder of the cassette.

29. The device of claim 28 wherein each reaction flow-way further comprises a sample input metering chamber within the cassette, such that:
(1) the sample input metering chamber of a reaction flow-way of the cassette is also in serial communication with one of the first cannulas of the input transfer sample bar;
(2) one or more reaction flow-ways are serially and respectively in communication via fluid exchange channels with the same number of sample input metering chambers;
(3) the fluid chambers of the one or more reaction flow-ways are in communication via fluid exchange channels, wherein the fluid chambers include supply chambers having reversibly sealed outlets for reagents, metering chambers for samples, or reaction chambers; and
(4) at least one of the fluid chambers is within the sample transfer/storage strip.

30. The device of claim 29, wherein the separable sample transfer/storage strip transfers and stores nucleic acid extracted from multiple samples separately from one another.

31. The device of claim 29, wherein at least one of the pump actuators comprises a foot-pad pump with foot-pads designed to push on the supply chambers to open the reversibly sealed outlets and pump fluid into the fluid exchange channels.

32. The device of claim 31, wherein each of the supply chambers is collapsible upon evacuation and fillable from a vacuum-collapsed state to a defined volume.

33. A method for extracting nucleic acid from a biological sample using the device of claim 1, comprising providing the device of claim 1 for nucleic acid extraction from one or more biological samples and extracting nucleic acid from a biological sample via the cassette.

34. The device of claim 1, further comprising a movable input transfer sample bar attached to the cassette.

35. The device of claim 34, further comprising:
(1) one or more sample entry ports located on the input transfer sample bar that are serially and respectively in communication with the same number of input sample storage reservoirs via sample input channels, and one or more second cannulas connected to a connector, wherein the sample entry ports and second cannulas are connected one each to sample containers, and wherein the input sample storage reservoirs are located in the cassette;
(2) one or more reaction flow-ways serially and respectively in communication with the same number of sample input storage reservoirs;
(3) fluid exchange channels via which the one or more reaction flow ways communicate with the same number of sample input storage reservoirs;
(4) fluid chambers in communication with the fluid exchange channels, wherein fluid chambers are supply chambers for reagents, reservoirs for samples, or reaction chambers, and wherein the supply chambers store and deliver to a reaction flow-way a lysis reagent, microparticles in a buffer, or buffer alone for nucleic acid extraction; and (5) valves for controlling the flow of fluids in the fluid exchange channels; wherein the sample transfer/storage strip includes at least one of the fluid chambers that is in communication with a reaction flow-way via one of the fluid exchange channels.

36. The device of claim 35, wherein the input transfer sample bar comprises a first cannula that is a sample entry port and connects a sample container to a sample input channel and a second cannula connects the same sample container to the connector upon movement of the input transfer sample bar and engagement of same with the sample container.

37. The device of claim 36, wherein at least one of the supply chambers has a releasable seal blocking an outlet or outlets from the supply chamber into the fluid exchange channels of the reaction flow-ways.

38. The device of claim 37, wherein each of the supply chambers is collapsible upon evacuation and fillable from a vacuum-collapsed state to a defined volume.

39. The device of claim 38, wherein the lysis reagent comprises microparticles.

40. The device of claim 39, wherein the microparticles comprise a compound that has specific affinity for nucleic acid or is paramagnetic.

41. The device of claim 40, wherein there are two or more sample entry ports and two or more reaction flow-ways.

42. The device of claim 41, wherein the separable sample transfer/storage strip transfers and stores nucleic acid extracted from multiple samples separately from one another.

43. The device of claim 42, wherein the separable transfer/storage strip is connected to the remainder of the cassette, which, upon being separated, seals both the strip and the remainder of the cassette.

* * * * *